(12) United States Patent
Ansari et al.

(10) Patent No.: US 10,557,168 B2
(45) Date of Patent: Feb. 11, 2020

(54) SENSING APPARATUS FOR AMPLIFICATION AND SEQUENCING OF TEMPLATE POLYNUCLEOTIDES AND ARRAY FOR AMPLIFICATION OF TEMPLATE POLYNUCLEOTIDES

(71) Applicant: DNAE Group Holdings Limited, London (GB)

(72) Inventors: Zahid Ansari, London (GB); Krishna Amin, Stockbridge, GA (US); Ginny Jorgensen, Sale (GB); Kurt Kolb, Burnaby (CA); Daniel Morley, London (GB); Alpesh Patel, London (GB); Samuel Reed, London (GB); Leila Shepherd, London (GB); Christofer Toumazou, London (GB)

(73) Assignee: DNAE Group Holdings Limited, London (GB)

( * ) Notice: Subject to any disclaimer, the term of this patent is extended or adjusted under 35 U.S.C. 154(b) by 0 days.

(21) Appl. No.: 16/393,027

(22) Filed: Apr. 24, 2019

(65) Prior Publication Data

US 2019/0249246 A1    Aug. 15, 2019

Related U.S. Application Data

(63) Continuation of application No. 15/494,832, filed on Apr. 24, 2017, now Pat. No. 10,316,363, which is a continuation of application No. 14/415,873, filed as application No. PCT/GB2013/051930 on Jul. 18, 2013, now abandoned.

(30) Foreign Application Priority Data

Jul. 18, 2012    (GB) .................................. 1212775.9

(51) Int. Cl.
| | | |
|---|---|---|
| *C12P 19/34* | (2006.01) | |
| *C12Q 1/6874* | (2018.01) | |
| *C12Q 1/6869* | (2018.01) | |
| *B01L 7/00* | (2006.01) | |

(52) U.S. Cl.
CPC .............. *C12Q 1/6874* (2013.01); *B01L 7/52* (2013.01); *C12Q 1/6869* (2013.01); *B01L 2200/147* (2013.01); *B01L 2300/0627* (2013.01); *B01L 2300/123* (2013.01); *B01L 2300/1827* (2013.01)

(58) Field of Classification Search
None
See application file for complete search history.

(56) References Cited

U.S. PATENT DOCUMENTS

| | | | |
|---|---|---|---|
| 6,203,683 | B1 | 3/2001 | Austin et al. |
| 7,649,358 | B2 | 1/2010 | Toumazou et al. |
| 7,686,929 | B2 | 3/2010 | Toumazou et al. |
| 7,888,015 | B2 | 2/2011 | Toumazou et al. |
| 7,948,015 | B2 | 5/2011 | Rothberg et al. |
| 8,114,591 | B2 | 2/2012 | Toumazou et al. |
| 8,685,228 | B2 | 4/2014 | Toumazou et al. |
| 8,698,211 | B2 | 4/2014 | Toumazou et al. |
| 2004/0134798 | A1 | 7/2004 | Toumazou et al. |
| 2005/0079510 | A1* | 4/2005 | Berka ............... B01L 3/502707 506/16 |
| 2008/0032295 | A1 | 2/2008 | Toumazou et al. |
| 2008/0176290 | A1 | 7/2008 | Joseph et al. |
| 2008/0265985 | A1 | 10/2008 | Toumazou et al. |
| 2009/0127589 | A1 | 5/2009 | Rothberg et al. |
| 2010/0137143 | A1 | 6/2010 | Rothberg et al. |
| 2010/0188073 | A1 | 7/2010 | Rothberg et al. |
| 2010/0197507 | A1 | 8/2010 | Rothberg et al. |
| 2013/0040863 | A1 | 2/2013 | Straus et al. |

FOREIGN PATENT DOCUMENTS

| | | |
|---|---|---|
| CN | 101743319 A | 6/2010 |
| CN | 101949883 A | 1/2011 |
| JP | 2007-535892 A | 12/2007 |
| JP | 2010-513869 A | 4/2010 |
| JP | 2010-519914 A | 6/2010 |
| JP | 2010-193884 A | 9/2010 |
| JP | 2011-525810 A | 9/2011 |
| WO | 03/073088 A2 | 9/2003 |
| WO | 2006/005967 A1 | 1/2006 |
| WO | 2008/076406 A2 | 6/2008 |
| WO | 2008/107014 A1 | 9/2008 |
| WO | 2011/123246 A2 | 10/2011 |

OTHER PUBLICATIONS

International Search Report of corresponding PCT/GB2013/051930 dated Oct. 14, 2013; 2pgs.
Jonghyun Go, et al., "The future scalability of pH-based genome sequencers: A theoretical perspective", in the Journal of Applied Physics, vol. 114, 2013, pp. 11 pgs.
Christofer Toumazou, et al., "Simultaneous DNA amplification and detection using a pH-sensing semiconductor system", in Nature Methods, vol. 10, No. 7, Jul. 2013, pp. 641-646 (7 pgs.).
Japanese Office Action dated Apr. 26, 2017, in connection with corresponding JP Application No. 2015-522173 (5 pgs., English translation only provided).

(Continued)

*Primary Examiner* — Kenneth R Horlick
(74) *Attorney, Agent, or Firm* — Maier & Maier, PLLC

(57) ABSTRACT

Provided is a sensing apparatus comprising a chip for integrated amplification and sequencing of a template polynucleotide in a sample. The apparatus comprises a chip with at least one ISFET in a well or chamber, amplification means for amplifying the template polynucleotide on a surface of said chip and comprising at least one heating means suitable for conducting amplification of the template polynucleotide at temperatures elevated with respect to room temperature, and sequencing means for sequencing the amplified template polynucleotide in said well or chamber. Methods of use are also provided.

14 Claims, 12 Drawing Sheets

(56) References Cited

OTHER PUBLICATIONS

Decision to grant dated Feb. 8, 2018 and Communication under Rule 73(3) EPC dated Oct. 20, 2017 in corresponding European Application No. 16 179 947.3; 7 pages.

* cited by examiner

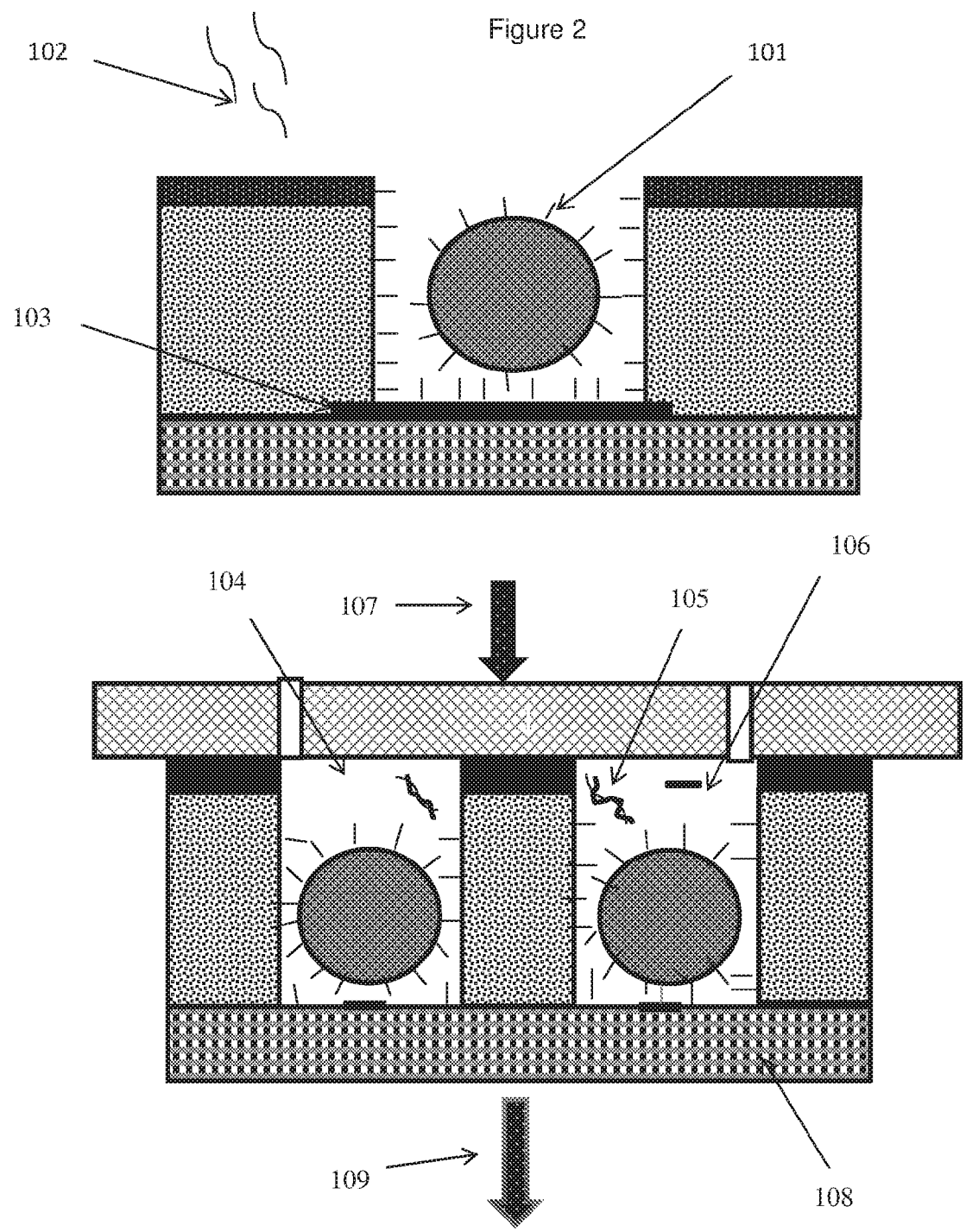

71. well/chamber
72. Top metal resistive heater
73. ISFET sensing gate
74. 2nd metal layer
75. 3rd metal layer
76. Polygate
77. Gate oxide
78. Dielectrics
79. P-substrate 81. ISFET sensor
82. Integrated sequencing chip
83. Temperature sensor

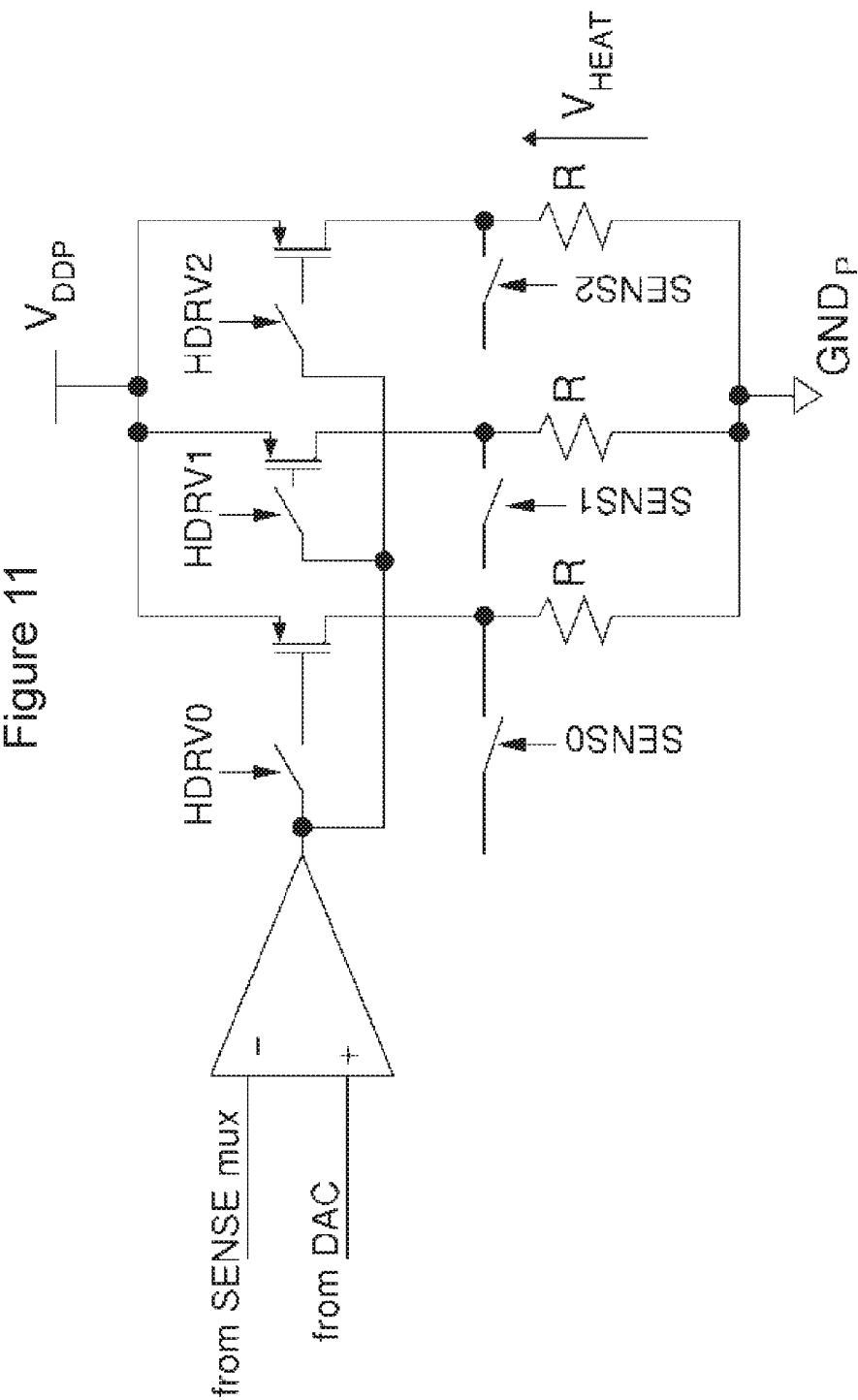

SENSING APPARATUS FOR AMPLIFICATION AND SEQUENCING OF TEMPLATE POLYNUCLEOTIDES AND ARRAY FOR AMPLIFICATION OF TEMPLATE POLYNUCLEOTIDES

CROSS-REFERENCE TO RELATED APPLICATIONS

This application is a continuation of U.S. patent application Ser. No. 15/494,832, filed Apr. 24, 2017, which issued as U.S. Pat. No. 10,316,363 on Jun. 11, 2019, which is a continuation of U.S. patent application Ser. No. 14/415,873, filed Jan. 20, 2015, now abandoned, which is a national phase Application of International Application No. PCT/GB2013/051930, filed Jul. 18, 2013, which claims priority to Great Britain Application No. 1212775.9, filed Jul. 18, 2012, the disclosures of which are incorporated by reference herein in their entireties.

BACKGROUND

Over the last two decades, there has been a rapid development in nucleic acid analysis, specifically in the field of nucleic acid amplification and DNA sequencing technology, with an increasing range of instrumentation now available. The conventional methods of detecting and analysing a nucleic acid sequence primarily rely on fluorescent nucleic acid intercalating dyes, fluorescent-labelled oligonucleotide probes, fluorescent- or radioactive-labelled nucleotides.

Subsequently, a new method of analysing nucleic acid synthesis and sequencing has been developed using a semi-conductor-based detection system such as an Ion Sensitive Field Effect Transistor (ISFET), see for instance our PCT publication WO 03/073088. An Ion Sensitive Field Effect Transistor-based platform, unlike conventional fluorescent-based nucleic acid analysis systems, does not require expensive optical instruments or dangerous radioactive isotopes for detection, thus making this platform a cost effective, safe and simple alternative for sequencing and nucleic acid amplification analysis.

Specifically, an ISFET, which measures ion concentrations in solution, has been employed to detect nucleotide incorporation into a nucleic acid strand by detecting the change in hydrogen ion (H+, proton) concentration resulting from the reaction.

Hydrogen ions are released during the nucleic acid polymerization reaction. For example, Equation I below demonstrates the release of hydrogen ion facilitated by DNA polymerase mediated hydrolysis of a single deoxynucleotide:

$$dNTP \rightarrow dNMP + PPi + zH+ \quad \text{(Equation I)}$$

wherein dNTP is a nucleoside triphosphate, dNMP is a nucleoside monophosphate, z is an integer or fraction describing the average number of protons generated per nucleotide turnover, $H^+$ is a proton and PPi is a Pyrophosphate (leaving group or reaction product).

The reaction can be driven to further produce more hydrogen ions by hydrolysing the pyrophosphate into two orthophosphates (Pi). Such a secondary chemical reaction is facilitated by pyrophosphatases and is depicted in Equation II:

$$PPi \rightarrow 2Pi + zH+ \quad \text{(Equation II)}$$

The workflow of current 'sequencing-by-synthesis' methodology can be broadly divided into template preparation, sequencing and detection, and data analysis. The first step, template preparation, usually involves clonally amplifying the template in order to achieve sufficient quantity of amplified template to confidently detect nucleotide incorporation signal during sequencing step. Currently, such clonal amplification step is usually performed in a compartment separate from the sequencing reaction and typically in a separate machine. However, such spatial separation of the two steps requires a skilled work force, high levels of hands on time, introduces incremental errors and may increase sample loss, thus decreasing the sensitivity of detection for sequencing and increasing costs.

To facilitate accurate sequencing, the standard practice is to amplify the nucleic acid. Various methods for amplifying nucleic acid are known. Indeed, PCT publication (WO2008/107014) discloses a method of monitoring qPCR using Solid-State pH Sensing, for instance an ISFET. Reaction monitoring is by means of detecting a change of pH resulting from proton release in the presence of a target (nucleic acid) sequence as amplification proceeds beyond a threshold number of cycles for the buffering capacity of a sample to be overcome. It does not disclose sequence detection via sequencing-by-synthesis, only detection of the amplification activity itself. WO2008/076406A2 also discloses various methods of amplification, such as bridge amplification, in the context of ISFETs.

Sequencing methods using ISFETs for determining are also known. US 2010/031398A1 discloses an apparatus for use in a method of sequencing, the apparatus comprising an array of microwells and sensors, which may be ISFETs. The sensors have a floating gate structure which in turn has a layer of protection material disposed over the floating gate from the analyte. The protection material has a thickness of up to about 600 Angstroms. Methods of manufacture are also provided. However, these sequencing methods operate as a distinct process on pre-prepared [colonies] of DNA.

Thus, it is an object of the present invention to provide an ion sensitive apparatus for amplification and sequencing, and a method for amplifying and sequencing nucleic acids which overcomes or mitigates the disadvantages posed by the existing methods of sequencing.

It is a further object of the invention to provide an ion sensitive apparatus for amplification and sequencing which overcomes the difficulties arising from the need to combine both amplification and subsequent sequencing without any spatial separation.

SUMMARY OF THE INVENTION

Thus in a first aspect, the invention provides a sensing apparatus comprising a chip for integrated amplification and sequencing of a template polynucleotide in a sample, the apparatus comprising:
  a chip with at least one ISFET in a well or chamber;
  amplification means for amplifying the template polynucleotide on a surface of said chip and comprising at least one heating means suitable for conducting amplification of the template polynucleotide at temperatures elevated with respect to room temperature; and
  sequencing means for sequencing the amplified template polynucleotide in said well or chamber.

According to a second aspect of the invention there is provided a method of determining the sequence of a plurality of template polynucleotides, the method comprising:
  providing the templates to a plurality of wells, each well exposed to an ISFET;
  optionally amplifying the templates;

immobilising at least one template within each well; then creating a clonal population within each well; and then sequencing the template colonies in the wells.

According to a third aspect of the invention there is provided a method of determining the sequence of a plurality of template polynucleotides, the method comprising:
providing the plurality of templates to a plurality of wells, each well exposed to an ISFET;
clonally amplifying the templates on a solid substrate in each well; and sequencing the amplified templates in the wells.

According to a fourth aspect of the invention there is provided a sensing apparatus for amplification and sequencing of a plurality of template polynucleotides, the apparatus comprising:
    a semiconductor chip having a plurality of ISFETs,
    a microfluidic structure defining a plurality of wells, wherein each well is exposed to at least one of the ISFETs;
    amplification means for amplifying the template polynucleotides and comprising at least one heating means suitable for conducting amplification of the template polynucleotide at temperatures elevated with respect to room temperature; and
    wherein the well is arranged to create a clonal population within each well;
    sequencing means for sequencing the template colonies in each well.

According to a fifth aspect of the invention there is provided a sensing apparatus for amplification and sequencing of a plurality of template polynucleotides, the apparatus comprising:
    a semiconductor chip having a plurality of ISFETs,
    a microfluidic structure defining a plurality of wells, each well exposed to at least one of the ISFETs;
    amplification means for immobilising and amplifying the template polynucleotides within the wells and comprising at least one heating means suitable for conducting amplification of the template polynucleotide at temperatures elevated with respect to room temperature; and
    sequencing means for sequencing the amplified template polynucleotides in the wells.

During amplification within the wells, it is particularly preferred that a removable seal is provided. This serves to seal off (i.e. contain and isolate) amplification reactions occurring in adjacent wells. The removable sealing caps prevent evaporation and cross contamination between reactions during amplification, thus providing optimal conditions for maximal amplification efficiency. Removable sealing caps can be a liquid or a solid material. Liquid sealing caps can be mineral oil or silicone oil. Solid sealing caps can be heat resistant silicone pads or thermoplastic elastomers (TPE).

Suitable reagents for both the amplification and the sequencing stages are provided and means for delivering them as part of the respective amplification and sequencing means are discussed herein. Nevertheless, it will be appreciated that the basic reagents include the template polynucleotide, a fluid environment with suitable buffers, a source of nucleotides (for amplification and/or sequencing) and a suitable polymerase for the respective reaction.

The sequencing means for sequencing the amplified template polynucleotide in said well or chamber preferably comprises a source of nucleotides for insertion, such as dNTPs. And the invention thus provides means to achieve this. These means may preferably include a source of nucleotides, preferably deoxynucleotide triphosphates (dNTPs). The source preferably comprises 4 or more separate supplies, one for each dNTP (dATP, dCTP, dGTP, dTTP and dUTP). In one embodiment, there may be one supply for each of dATP, dCTP, dGTP, dTTP and dUTP, thus allowing DNA or RNA templates to be sequenced by the same apparatus. The source or supply preferably also comprises a pump for said nucleotide. Suitable routing and control mechanisms are known; see for instance FIG. 8 and the accompanying description in US 2010/031398A1, hereby incorporated by reference.

Suitable amplification polymerases for thermocycling and isothermal amplification include but not limited to Taq polymerase, Pfu polymerase, Phusion polymerase, Vent polymerase, Bst polymerase, exo Klenow polymerase, phi29 DNA polymerase, and mutants and derivatives thereof. The amplification pols (polymerases) may be provided on the chip prior to addition of the sample or template nucleic acid, for instance by printing or spotting. Preferably, in that instance, they are also inactivated after the amplification is complete. Alternatively, they can be added to the site of amplification in/on the chip when required. Suitable pumps, routing and control means for this are envisaged as required.

Suitable sequencing polymerases (not limited to both RNA or DNA polymerase) include but are not limited to exo-Klenow fragment DNA polymerase I, T4 exo-, Therminator, Bst polymerase, phi29 DNA polymerase, and mutants and derivatives thereof. The sequencing pols (polymerases) may be provided on the chip prior to addition of the sample or template nucleic acid, for instance by printing or spotting. Preferably, in that instance, they are also inactivated during amplification and re-activated when amplification is complete. Alternatively, they can be added to the site of sequencing (i.e. the well) when required. Suitable pumps, routing and control means for this are envisaged if required.

Amplification may be by means of bridge amplification, Polymerase chain reaction, Nucleic Acid Sequence Based Amplification (NASBA; Deiman B et. al., 2002), Strand-displacement amplification (SDA; Andras S C, 2001), Rolling circle amplification (U.S. Pat. No. 5,714,320), and Loop Mediated Isothermal Amplification (LAMP), all of which are well-known techniques in the art.

Preferably, the ISFET monitors the amplification reaction. The ISFET is in any case positioned so as to be able to detect sequencing at or in a well, so the ISFET may also be employed to monitor amplification, when that occurs at said well too. In the alternative, the ISFET may be turned off during amplification to save power.

Monitoring the amplification reaction allows the system to determine when suitably large colonies of template are present in a well, which determination can be fed to a controller to change or stop the amplification process in a well or all wells.

In a further aspect of the invention, there is provided a method of determining the sequence of a template nucleic acid, the method comprising amplifying a template nucleic acid in a sample and sequencing the amplified nucleic acid in the present apparatus. Other preferred method steps are described above and generally herein, but it is preferred that the nucleic acid in the sample is fragmented prior to amplification to break it down into usefully sized portions. Large DNA molecules, for instance, can be sequenced in this manner, even whole genomes.

Preferably, the nucleic acid in the sample is amplified and subsequently sequenced in the same well or chamber.

In some embodiments, the sensing apparatus has at least one oligonucleotide immobilised within each well, which oligonucleotide is unbound to a polynucleotide but adapted to bind to the template polynucleotide.

In some embodiments, the sensing apparatus comprises a removable seal arranged to cover a surface of the microfluidic structure, thus substantially isolating each well from adjacent wells.

In some embodiments the solid removal seal is a flexible membrane or an adhesive such as a pressure sensitive adhesive.

In some embodiments, the apparatus is arranged such that the amplification of each template occurs in the same well as sequencing of that template.

In some embodiments, the surface of each well of the sensing apparatus is modified with means to immobilise oligonucleotides. Also preferable is a sensing apparatus wherein only a single oligonucleotide is available in each of the wells to hybridise with the template polynucleotide in the sample. In some embodiments, beads may be used as a surface for immobilisation of amplified nucleic acid.

The apparatus may comprise a heater wherein the heater is a resistive heating element integrated into the chip. In some embodiments a path formed from one or more metal layers.

In some embodiments, the method may further comprise the steps of:
providing the template to the wells in a ratio of one template to between 0.4 and 2 wells. In some embodiments one template to about every one well.
providing a seal to the wells to isolate adjacent wells during amplification of the template
removing the seal prior to sequencing of the amplified templates.

In some embodiments, the method may further comprise the steps of:
providing a single template binding site in each well;
providing a seal to the wells to isolate adjacent wells during amplification of the template; and
removing the seal prior to sequencing of the amplified templates.

The single template binding site may be on a bead. In some embodiments wherein either (a) the bead is bound to a surface of each well by a binding site only large enough to bind one bead or (b) said bead is sized so that only one such bead can fit into each well.

In yet another embodiment, the method may further comprise the step of controlling charges on electrodes exposed to each well to attract templates to each well. In some embodiments wherein the charge on individual electrodes in each well is removed or reversed upon detection of a template binding to a surface of that well.

In one embodiment, it is preferable that the oligonucleotides are sequence specific so as to bind one or more strands of a target template type to a single solid substrate.

The oligonucleotides immobilised on a surface of the well or within the well may be sequestered. In some embodiments by coating the oligonucleotides with wax. The sequestration of immobilised oligonucleotides may be removed by heating the wax. In some embodiments after washing unbound template from the wells.

It is preferable that the methods further comprise the step of providing to each well a plurality of beads having further binding sites for clonal amplification of the template bound in that well.

It is preferable that the methods further comprise the step of washing away unbound templates from the wells before sequencing.

According to a further aspect of the invention, there is provided a sensing apparatus comprising a chip for integrated amplification and sequencing of a template polynucleotide in a sample, the apparatus comprising a chip with at least one ISFET in a well or chamber; an amplification means for amplifying the template polynucleotide on a surface of said chip and comprising at least one heating means suitable for conducting amplification of the template polynucleotide at temperatures elevated with respect to room temperature; and a sequencing means for sequencing the amplified template polynucleotide in said well or chamber.

According to yet a further aspect of the invention, there is provided a method of determining the sequence of a template nucleic acid, the method comprising amplifying a template nucleic acid in a sample and subsequently sequencing the amplified nucleic acid, using the apparatus according to any preceding claim.

According to a further aspect of the invention there is provided a sensing apparatus for amplification and sequencing of a plurality of template polynucleotides, the apparatus comprising:
  a semiconductor chip having a plurality of ISFETs,
  a microfluidic structure defining a plurality of wells, each well exposed to at least one of the ISFETs;
  amplification means for immobilising and amplifying the template polynucleotides within the wells and comprising at least one heating means suitable for conducting amplification of the template polynucleotide at temperatures elevated with respect to room temperature; and
  sequencing means for sequencing the amplified template polynucleotides in the wells.

According to yet a further aspect of the invention, there is provided a method of determining the sequence of a plurality of template polynucleotides, the method comprising:
providing the plurality of templates to a plurality of wells, each well exposed to an ISFET;
clonally amplifying the templates on a solid substrate in each well; and
sequencing the amplified templates in the wells.

BRIEF DESCRIPTION OF THE DRAWINGS

FIG. 11 is a schematic of a heater driver circuitry according to one embodiment of the invention.

DETAILED DESCRIPTION

Figure 1:
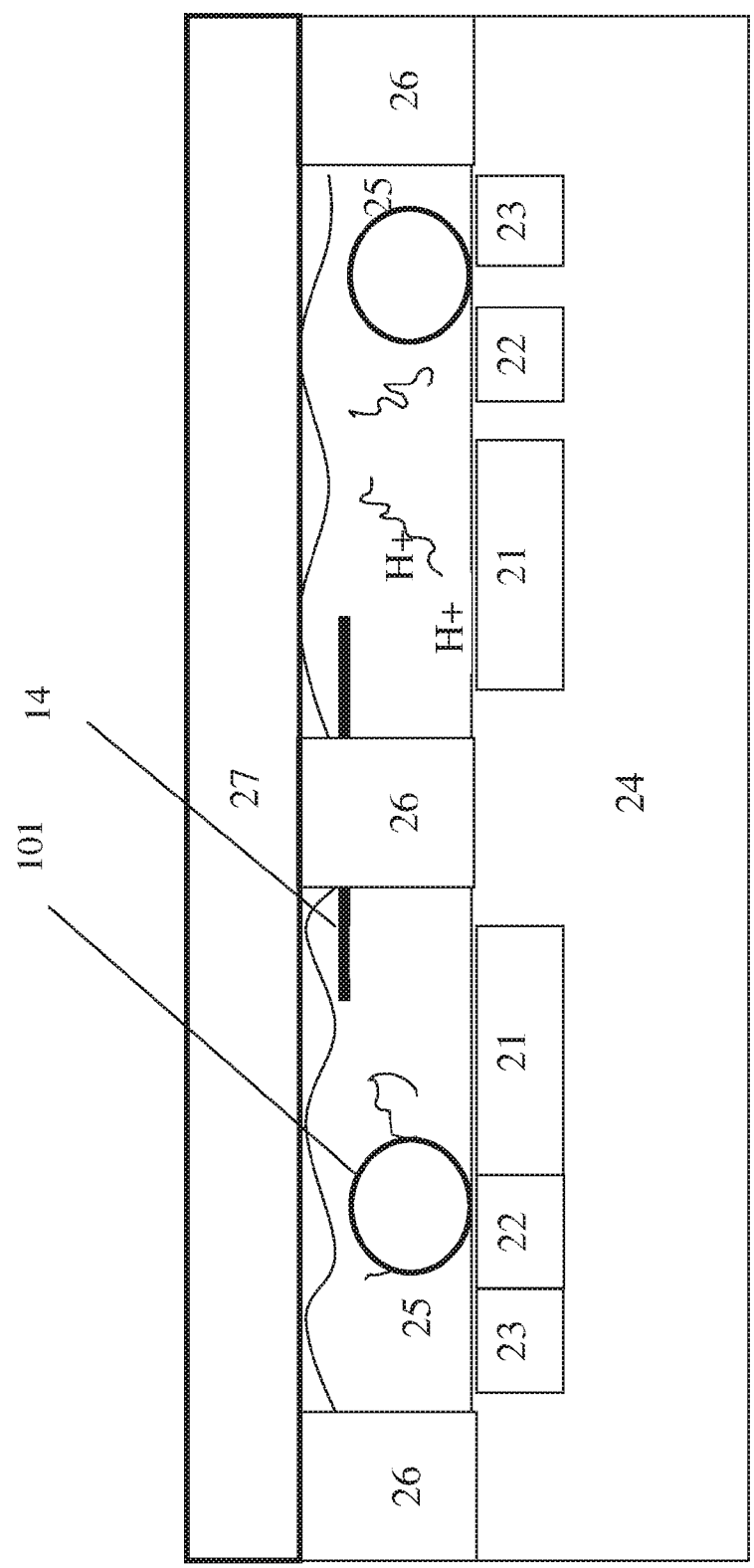
FIG. 1 is a profile view of pH detection system.
Figure 2:
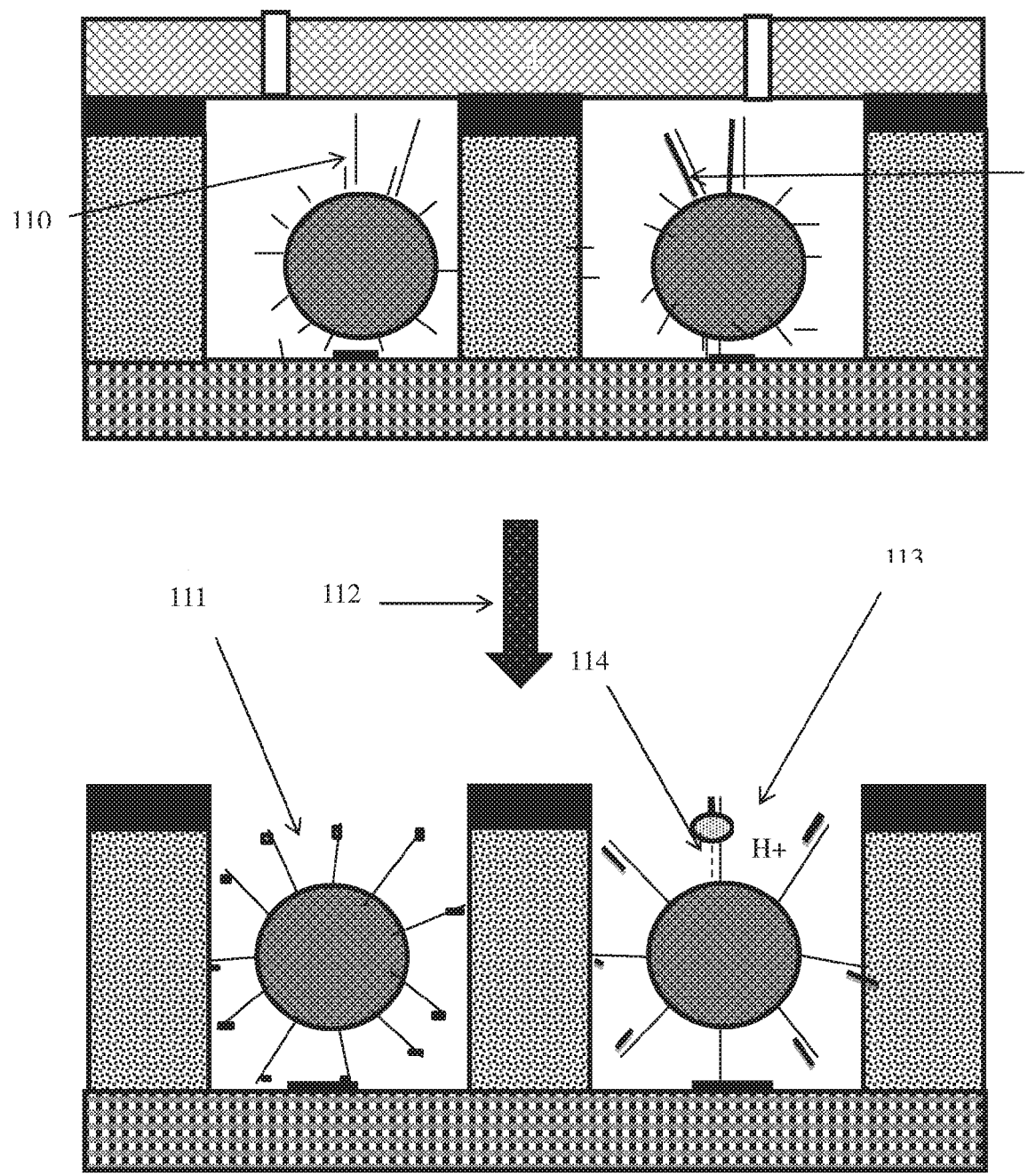
FIG. 2 is a schematic of one embodiment of integrating nucleic acid amplification and sequencing in the same well.

The inventors have devised a method and apparatus to combine the two (amplification and sequencing of a target nucleic acid), thus providing an integrated device. One advantage of this is that it may speed up the provision of the output, namely the sequence of the target nucleic acid. Another advantage is that an integrated system addresses a number of challenges which used to be solved by manual processes and lab tools. In addition, such integration may increase the speed of the workflow with minimal hands-on time and decrease sample loss. Moreover, with an integrated system that is further automated, it will be possible to shift the applications for sequencing from specialist scientists in laboratories to a more commercial environment for use by professionals, nurses or technicians.

However the difficulty in combining the steps of amplification and sequencing is that the optimal conditions for each can be quite different and there is very little synergy to be realised between the instruments. Normally each of these steps requires a complex instrument, each instrument optimised mechanically, electrically and biochemically to perform that function. For example, emulsion PCR for amplification requires a mix of oil and aqueous fluids containing unlabelled nucleotides and biochemistry/apparatus to detect beads having only a single clonal population. Conversely the sequencing step requires biochemistry with labelled nucleotides and apparatus to detect fluorescence. Moreover the disposable portions used in the tests are often quite simple (e.g. a glass slide) with all of the functionality provided by the instruments.

In one respect the present inventions provides a method and apparatus that brings functionality to the disposable portion in order to reduce the complexity of the fixed instrument and combine process steps by using overlapping chemistry and apparatus.

It will be appreciated that the term nucleic acid includes polynucleic acids such as DNA or RNA and in either single stranded or double stranded form, as appropriate, any of which are preferred.

The disclosure of our publication WO2008/107014 is hereby incorporated by reference to the extent that it is useful in the amplification of polynucleic acids.

Although the invention has been described in terms of preferred embodiments as set forth above, it should be understood that these embodiments are illustrative only and that the claims are not limited to those embodiments. Those skilled in the art will be able to make modifications and alternatives in view of the disclosure which are contemplated as falling within the scope of the appended claims. Each feature disclosed or illustrated in the present specification may be incorporated in the invention, whether alone or in any appropriate combination with any other feature disclosed or illustrated herein.

The present invention provides an ion sensitive apparatus and method for semiconductor sequencing. This approach enables both clonal amplification as well as sequencing of the clonally amplified nucleic acid (e.g. DNA) to take place in the same well. Thus, there is preferably provided a fully integrated apparatus that provides the means for a sample-to-sequencing result system.

The apparatus allow simultaneous clonal amplification (preferably PCR, bridge amplification or isothermal amplification) of a nucleic acid template (which includes a plurality of different nucleic acid templates generated, inter alia, by fragmentation). The clonal amplification may occur in a well that is spatially separated (i.e. discreet) on a sensing platform. The invention further provides means for performing amplification of the plurality of nucleic acid templates that are spatially separated (e.g. a microwell) and sealed, followed by preparing said amplified plurality of DNA in the same well for subsequent sequencing-by-synthesis reaction. Where a plurality of different nucleic acid templates are used, the invention also provides means for distributing a single template in each well for amplification. The invention also provides a means for distributing a single species of template in each well for amplification.

Semiconductor Chip

The FET functions by producing an exchange of charged ions between the surface of the chemical sensitive layer and the reacting medium (i.e. the enzyme/electrolyte interface):

$$SiOH \leftrightarrow SiO^- + H^+$$

$$SiOH_2^+ \leftrightarrow SiOH + H^+$$

$$SiNH_3^+ \leftrightarrow SiNH_2 + H^+$$

The inclusion of silicon nitride, for example, is advantageous because it provides increased and faster sensitivity to changes of pH than would be obtained in the absence of the silicon nitride. In addition the silicon nitride helps to protect the FET from hydration and charge migration.

A non-Nernstian response accounts for the immediate sensitivity of the FET, arising from rapid proton dependant binding and unbinding of charged ions at the insulating gate silicon nitride surface, which results in a reproducible variation in the voltage drop across the silicon nitride layer. The variation of the voltage drop across the silicon nitride layer correlates with changes of pH. The voltage drop is monitored using instrumentation circuitry, thereby allowing the detection of individual nucleotide insertions. The measured voltage is referred to as the threshold voltage.

In one embodiment shown in FIG. 1, the ion sensitive apparatus(es) 21 may be a plurality of ISFETs on a CMOS microchip 24, having thereupon microfluidic wells 25 defined by manifold 26. The CMOS microchip may also contain one or more heaters 22 and temperature sensors 23. The nucleic acid synthesis reaction mixture containing nucleic acid template, one or more polymerase and one or more nucleotides is added to the wells exposed to the ISFET(s). Each ISFET outputs an electrical signal which is monitored by a signal processor. The ISFET preferably comprises a passivation layer and or sensing layer. These can be functionalized to be sensitive to protons. The sensing layer(s) can be made of metal oxide or metal nitride selected from among the group consisting of Al2O3, SiO2, Si3N4, Al2O3, Ta2O5, HfO3, WO3, and a super-Nernstian material or a mix of these materials or a laminate structure having different material layers, each layer ranging from 1 nm to 50 nm thick. As the nucleotides are hydrolysed and incorporated into the growing nucleic acid chain, protons will be released and be detected by the signal processor as a change in the electrical output of the ISFET. The change in electrical signal of the ISFET is indicative of nucleotide incorporation during nucleic acid synthesis. The apparatus may contain a removable sealing cap 27. A solid sealing cap may be coupled to mechanical actuator lifting to an open position and lowering to a sealed position (see below for further description of different types of sealing cap for the wells).

Preferably, each ISFET generates a normalised output signal from the difference between the ISFET signal and a reference signal. Preferably, the reference signal is derived from an ISFET or FET located on the chip in a different well where at least one of the dNTP, enzyme or primers is absent in the mixture, thus no reaction will proceed. Therefore, any common drift or noise on the chip will be cancelled by taking the difference between these signals.

Figure 7:
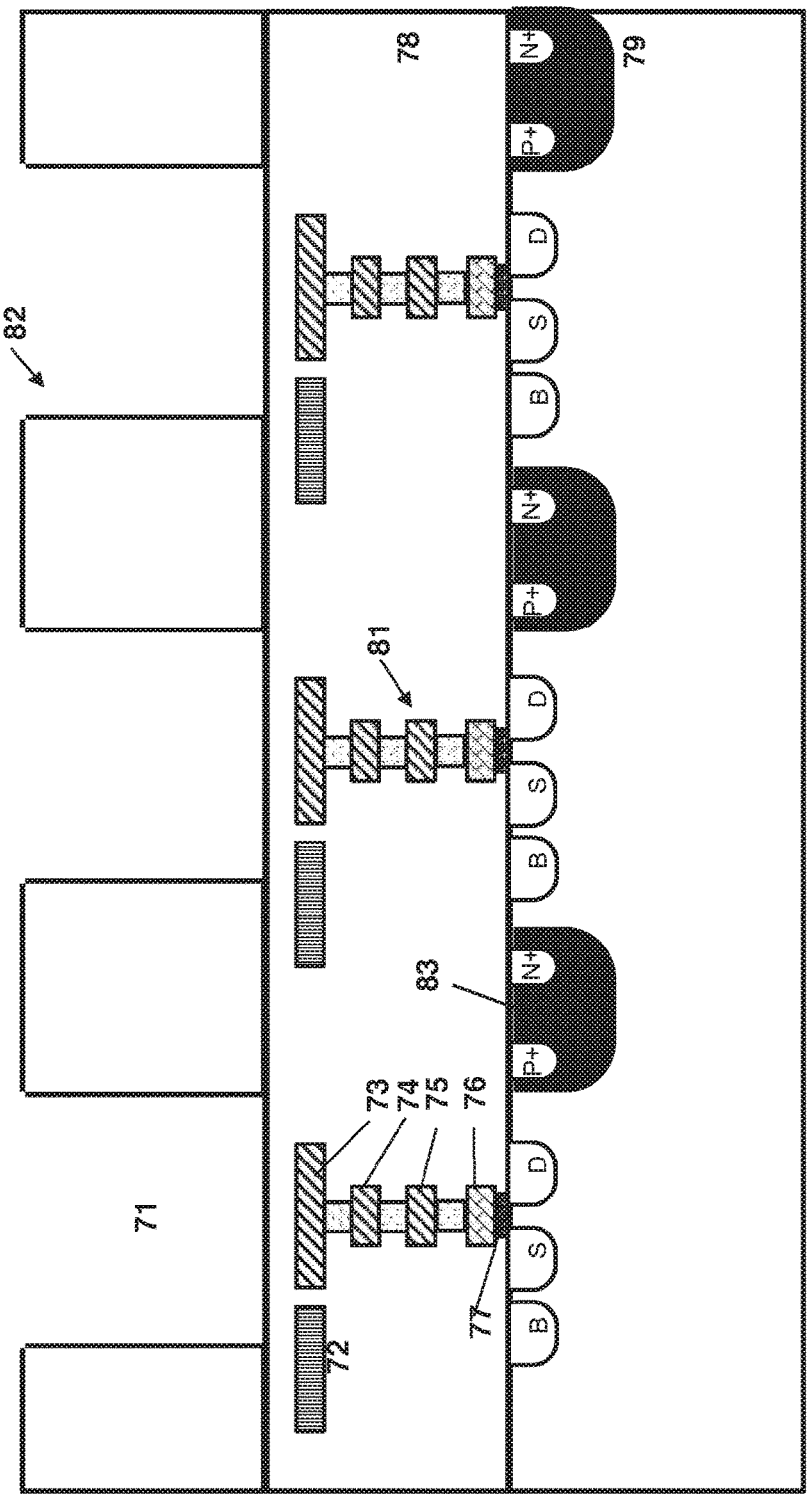
FIG. 7 is a cross-sectional view of the chip taken generally at line AA of FIG. 6, showing parallel linear heating elements, temperature sensors and ISFET sensors.

FIG. 7 shows an ISFET with a floating gate and sensing layer made of Silicon Nitride, which is exposed to the reaction mixture.

The Apparatus preferably comprises a microfluidic structure, which may be integrated with, or coupled to the chip. Microfluidics deals with the precise control and manipulation of fluids that are geometrically constrained to a small scale, usually µl or pl volumes and devices for such use are well known in the art. The microfluidic structure may provide walls, channels, and manifolds which transport and contain fluids. A simple structural example would be a moulded plastic piece with cavities provided to define the channels and wells. Alternatively the structure may be a planar substrate with portions punched through to define sides of the channels and wells, to thereby form a substrate. This substrate is coupled to the chip surface defining the bottom of the well or channel. Such structures are disclosed by PCT/GB2013/050832, portions related to the Sensor Cartridge incorporated herein by reference. The structure may also be built up in the semiconductor foundry as an extra layer on top of the semiconductor layer and metal wiring layers, whereby the wells and channels are defined by etching through the microfluidic layer. Such structures are disclosed by GB1218356.2, incorporated herein by reference. The substrate or structure may also be considered to be part of, or form all of, a microfluidic device. As such, the present apparatus may be considered, in some embodiments, to comprise a microfluidic device.

The purpose of the wells is to contain the reagents and expose reaction by-products to the sensing layer of an ISFET. The number of wells can be on the order of 10^8 or more for thorough genome sequencing or on the order of at least 100 for general bacterial identification. Preferably there are at least 100 wells, more preferably at least 1000 wells, most preferably at least 100, 000 wells.

A liquid removable seal (sealing cap) can be introduced into the apparatus (e.g. the microfluidic device) by means of a pump/pressure source and one or more controllable valves that control of entry of reagents. An example of such means (pumps/pressure source and control valves) is described in U.S. Pat. No. 7,948,015B2 and US2010/0301398A1, hereby incorporated by reference.

In particularly preferred embodiments where an oil (preferably a mineral oil) is used as a removable seal, also referred to herein as a sealing cap, the oil can be removed by several rounds of alternating washes of organic solvent and pre-sequencing buffer. Alcohols such as methanol, isopropanol, ethanol, isobutanol are suitable organic solvents. Others such as diethyl ether can be used. Examples of organic solvents for removing mineral oil can be found in U.S. Pat. No. 7,842,457B2, hereby incorporated by reference.

In a preferred embodiment, beads are used. They may function as a surface for capturing template(s) for sequencing, in which case we may term them capture beads. They can also aid in location of amplified template, for instance, into wells. The beads used herein may be fabricated from any number of known materials. Examples of such materials include: inorganics, natural polymers, and synthetic polymers. These may include but not limited to cellulose, cellulose derivatives, glass silica, cross-linked dextrans (e.g., SEPHADEX™) and agarose gel. Additional examples are further described in U.S. Pat. No. 7,842,457B2, hereby incorporated by reference, and are known to those of skill in the art. The beads suitable for covalent attachment may be magnetic or non-magnetic in nature. In a preferred embodiment, the beads are streptavidin-coated polystyrene beads. The beads are also preferably polystyrene.

The terms capturing and immobilisation may, in general, be used interchangeably. For the purposes of the present application, we have used capture sites to cover immobilised oligonucleotides, which in turn cover primers (or probes) attached to a surface.

Preferably, the capture beads and well sizes will be relatively sized so as that only one bead will fit into the well, although the well may accommodate other components such as reagents, packing beads and beads to continue immobilising copies of a given template.

Oligonucleotides may be attached to the solid support (e.g., beads or walls of the well) via chemical groups or by further oligonucleotides that are bound to the surface of the support. The attachment of the oligo- or poly-nucleic acid to the bead can be performed by means known in the art. For example, covalent chemical attachment of nucleic acid to the beads can be accomplished using standard coupling agents such as water soluble carbodiimide, which can be used to link the 5'-phosphate of a DNA sequence to amine-coated beads through a phosphoamidate bond. Whilst there are various definition for the term oligonucleotide in the prior art, in the context of this application, it should be taken to mean a short stretch of nucleic acids which may be attached to a solid support to act as a link for binding (anchoring) nucleic acid templates in the wells. The terms oligonucleotides and primers are used interchangeably. The oligonucleotides hybridise to template nucleic acids.

The template to be amplified and sequenced ideally will be ssDNA or RNA. This is preferable when hybridising to the immobilized oligonucleotide, however, double stranded DNA may be envisaged wherein it contains "sticky ends" resulting from, e.g. restriction enzyme digestion. The orientation-specific sticky end will hybridise to the oligonucleotide immobilized on beads or solid support and ligase can be added to form covalent bond between template and the oligonucleotide.

The nucleic acid template may be of any size amenable to in vitro amplification. In the preferred embodiment, the template is about 20-500 base pairs in length.

The template may be attached (for instance by ligation or covalent bonding) to a solid support within the well before, during or after amplification. The templates or amplified templates are at some step flowed to the wells and it is within the well that a clonal population of nucleic acids are created, one colony for each well. As will be described more below, this population can be created by immobilising a single template within the well and amplifying it or immobilising a population of identical templates within the well. This is in contrast to prior techniques which create a clonal population bound to a bead outside the well and transport the bead to the well, It is also particularly preferred that the apparatus, for instance the chip or microfluidic structure, comprises one or more wells and the amplification and sequencing reactions (for each template) occur "in the same well."

The heating means comprises a heater. Preferably there is a temperature sensor. It may also preferably comprise a controller providing a control loop between the temperature sensor(s) and heater(s). For example, when using Bst polymerase for amplification, the heating means raises the temperature to around 50 degrees Centigrade, preferably up to 60 or even 65 degrees C., 60-65 being most preferred for isothermal amplification using Bst polymerase. Higher temperatures are envisaged, for instance up to 70, 80 or even 90 degrees, and 84-98 degrees C. is particularly preferred in some instances where thermocycling is required. What is important is that the temperature is optimal for the relevant polymerase, or at least not above the threshold for denaturation of the relevant polymerase.

The chip can be exposed to an external thermal environment where the active heating and cooling happens and transfer that flux cycle to the chip On-Chip Heating Most preferably, the heating means comprises an on-chip heating element and, optionally, also an on-chip temperature sensor and/or an on-chip temperature control circuitry. Furthermore, it is also preferred that the heater is a resistive heating element integrated into the chip.

Figure 3:
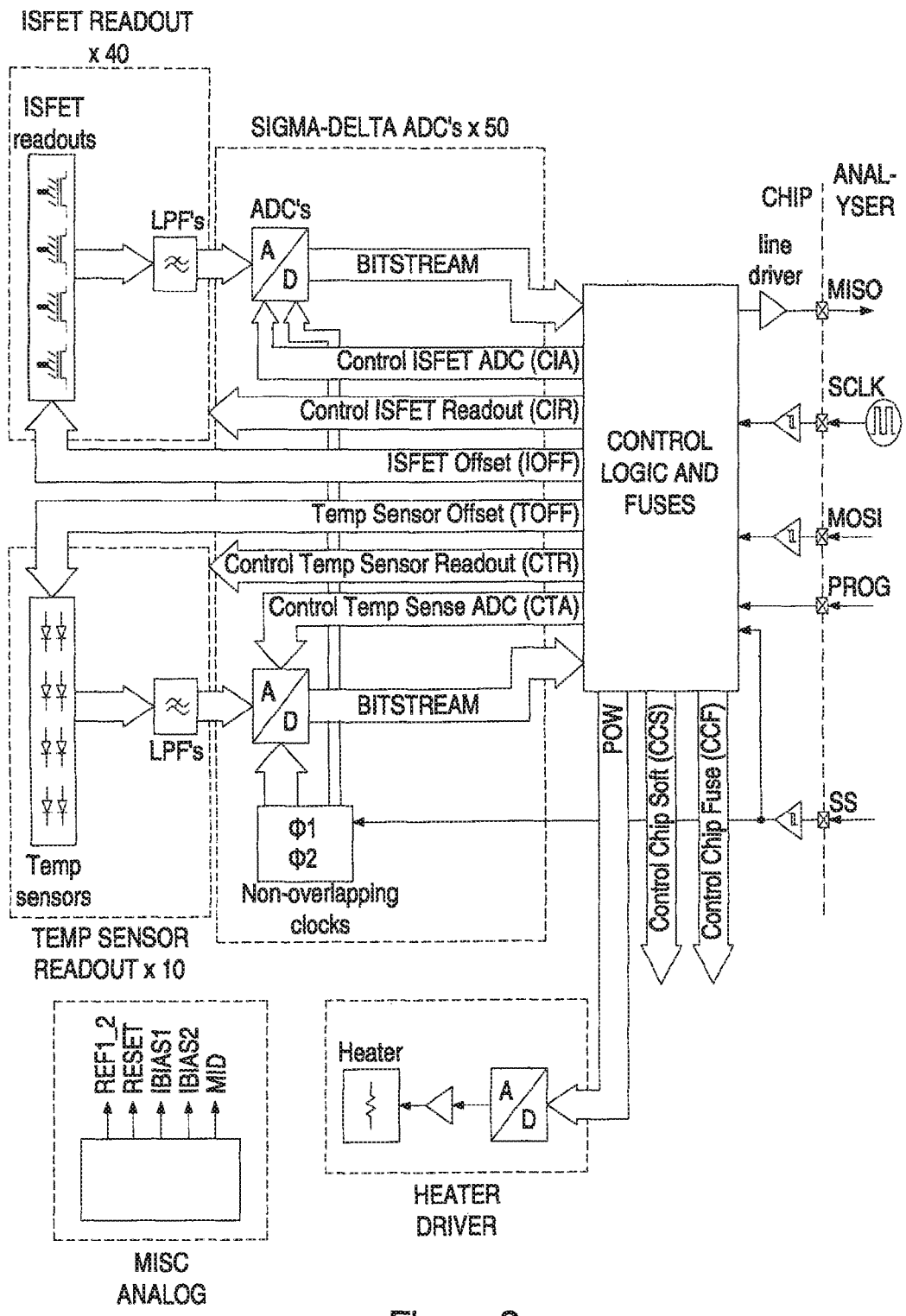
FIG. 3 is a schematic of one embodiment of a CMOS fabricated IC with ISFETS, temperature sensors, heater, signal processing circuitry, and analogue to digital conversion.

In one embodiment, there may be one heater and one sensor allocated per well. Alternatively, one heater may be sufficient for heating an area that contains between 10 and 100 wells. The arrangement of heaters/sensors to wells will depend on the density of wells in an array. In another embodiment, the heater may be parallel wires that run along the columns of the wells and are situated beneath the wells or in between wells. In another embodiment, the heater may be a transistor and may have both heating and temperature sensing functionalities (a heater-sensor hybrid). In yet another embodiment, the heating may be provided by thermoelectric effect (Peltier effect) such as thermolelectric heat pumps coupled to a surface of the semiconductor chip. The heating elements described in the present invention are implemented in a sensor system with analogue and digital control circuitry (FIG. 3). Further description of on-chip heaters, temperature sensors and temperature control circuitry can be found in U.S. Pat. No. 7,888,015B2.

Figure 6:
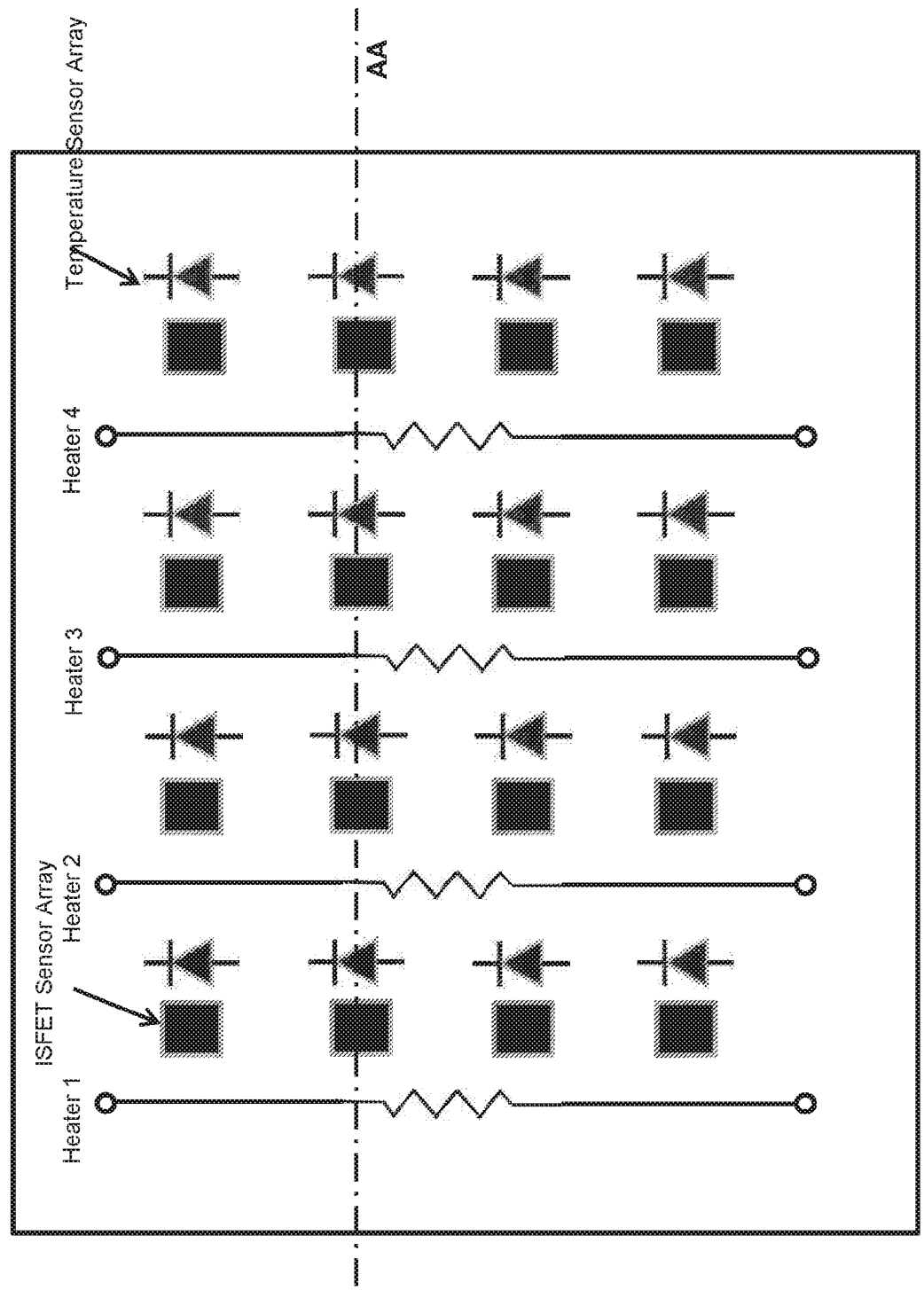
FIG. 6 is a top plan view of a chip according to one embodiment of the invention, showing parallel linear heating elements, temperature sensors and ISFET sensors.
Figure 8:
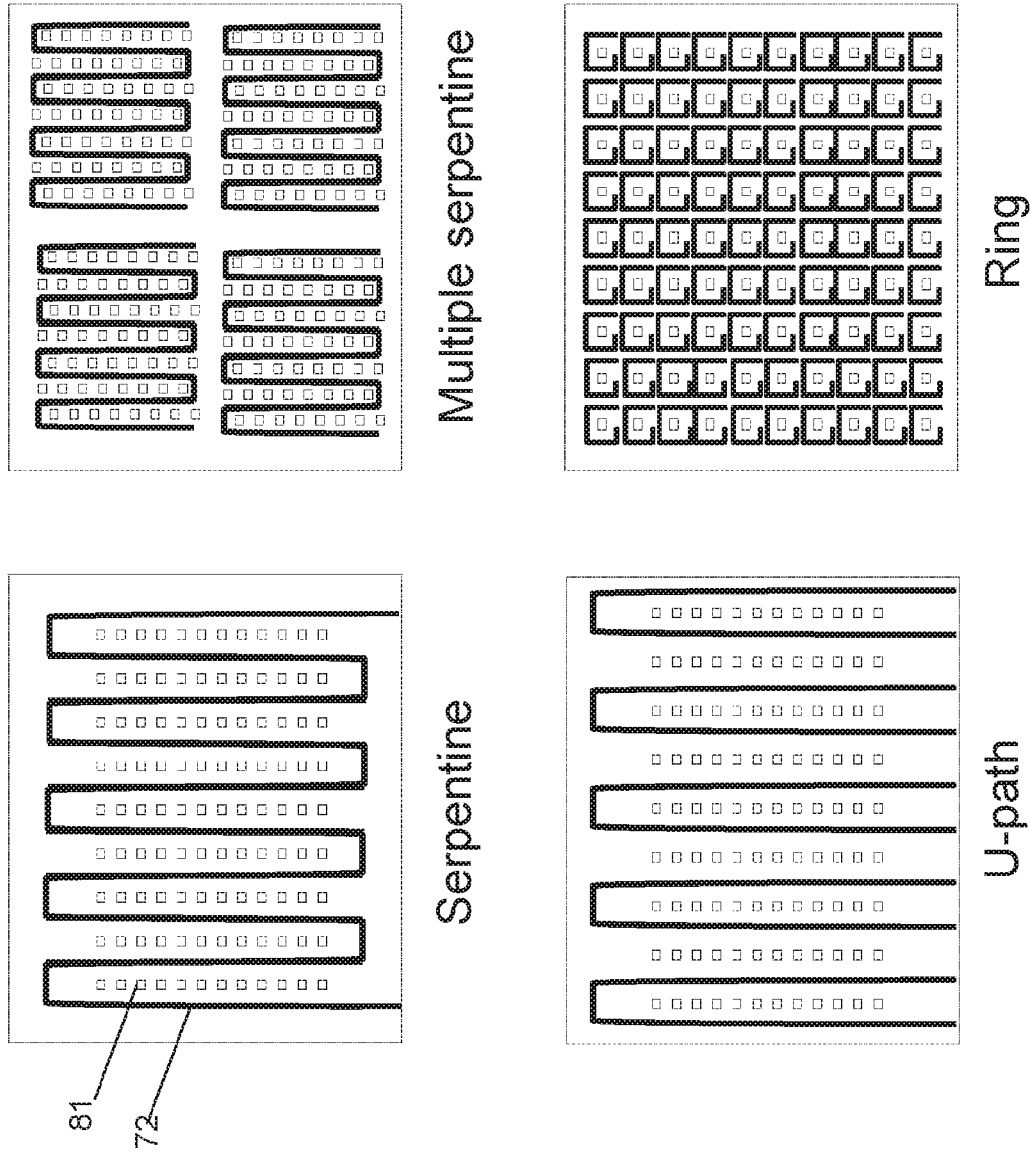
FIG. 8 illustrates examples of various arrangements of heater elements relative to ISFET sensors.
Figure 9:
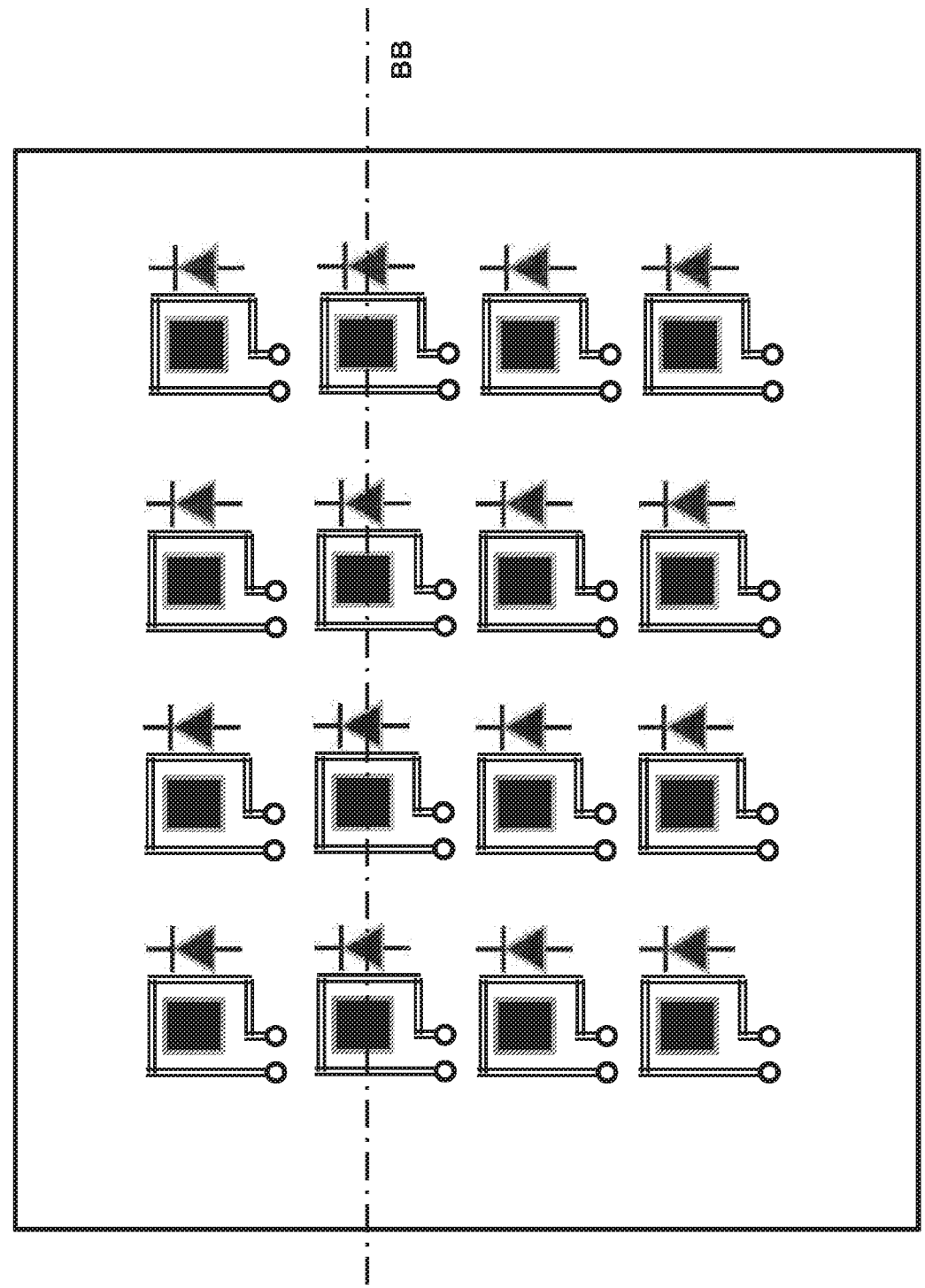
FIG. 9 is a top plan view of a chip according to one embodiment of the invention, showing pixelated heating elements, temperature sensors and ISFET sensors.
Figure 10:
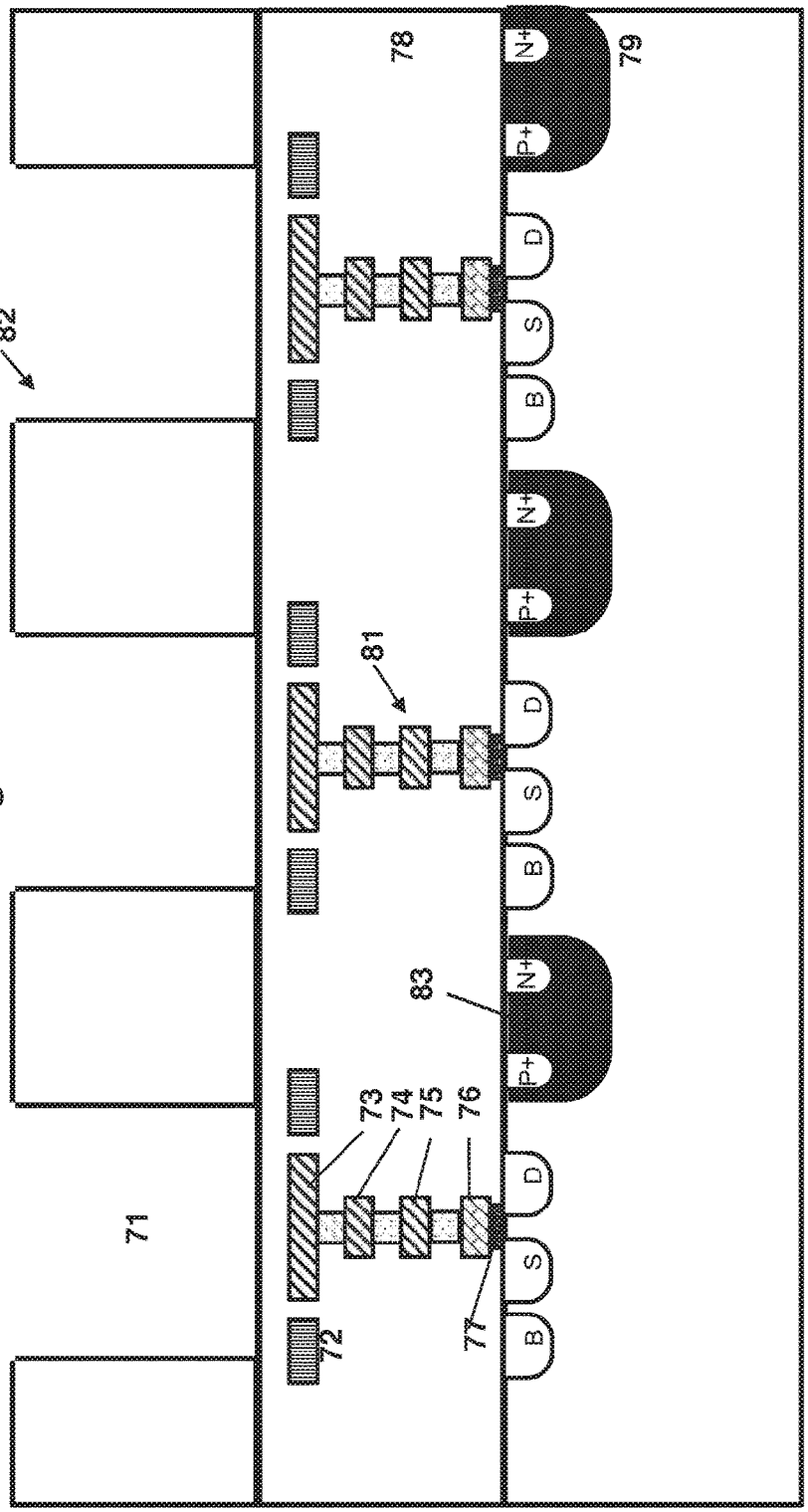
FIG. 10 is a cross-sectional view of the chip taken generally at line BB of FIG. 9, showing pixelated heating elements, temperature sensors and ISFET sensors.

In some embodiments, the chip is a CMOS (Complementary Metal-Oxide-Semiconductor) chip. In one embodiment, the top metals of the metal layer of the CMOS chip can function as heaters. Preferably, the top metals function as resistive heaters wherein the resistive heaters may comprise parallel linear heating elements homogenously distributed across the whole chip as exemplified in FIG. 6 and FIG. 8 or across a portion of the chip. The homogenous distribution of heating elements enables a uniform heating across the chip surface. The resistive heating element may be in the shape of a serpentine, a U, a ring, a spiral, a polygon or a straight line (as shown for example in FIG. 8). In some embodiments, the chip comprises an array of pixelated resistive heating elements wherein the pixelated resistive heating elements may adopt a ring shape, a spiral shape or a polygon shape.

In some embodiments, the chip comprises a guard ring. The guard-ring (i.e. electro static shield) of the chip may function as a heater. Normally the entire shield path is coupled via circuitry to the power supply to provide shielding, but during heating the path is reconfigured to connect to drive circuitry to pass a current through the path.

The placements of one or more heating elements designed relative to the ISFET sensors, the size of the sensor array and the chip surface such that the heat generated can provide uniform heating across the die surface and to each individual ISFET sensor. In such embodiments, the heating elements are in the plane of the top metal layer of the metal layers of the CMOS chip. Alternatively, if a temperature gradient across the die surface is desired, each individual heating element can be turned on and off to achieve the effect. Such attributes can enable, for example, PCR amplification of reaction mixtures requiring different annealing temperatures to be performed simultaneously on the chip.

The arrangements of heating elements across the chip are dependent on the number and the density of ISFET sensors per chip, as well as the number of ISFET sensors proximal to each well. In one embodiment, a row (or column) of ISFET sensors and wells is sandwiched between two parallel heating elements. In another embodiment, a plurality of rows (or columns) of ISFET sensors and wells are sandwiched between two parallel heating elements. Similarly, a heating element may surround one or more ISFET sensors and/or wells.

The number and the length of parallel heating elements across the chip will depend on the size of the chip. For example, for a 5 mm×5 mm chip, the heating area can be made up of 8 parallel heating elements with a mean heater resistance of 50 ohms for each heating element, which generates 4 W/cm2 of power for heating via heaters only.

A heater driver for the heaters may be provided. This heater driver can take an 8-bit POW register value as its input and translate it to a constant output voltage across the heaters. In one embodiment, the heaters can be driven in Class A mode by continuously controlling the value of POW between 0 and 255. In another embodiment, the heater can be driven in Class D mode by controlling the duty cycle (PWM mode) or by controlling the density of a stream of pulses which turn the heater on (Bitstream mode). The main advantage of such design is to provide flexibility for the heaters to be controlled in order to achieve target temperature profile at different thermal environment.

Heater Material:

The materials of the heater metals one or more of Aluminium, Copper, Tungsten, or other common metal composition or alloy. The choice of material is highly dependent on the manufacturing process the chip.

Heater Driver Circuit

In one embodiment, the heater driver comprises at least one individual driver stage, which can be selectively turned on/off by setting a heater driver selection register (HDRV). The heater paths (represented as R in above) are distributed across the chip. In such configuration, only one driver stage is run in a true closed loop by closing the "SENSE" connection to the negative feedback of the heater driver opamp. Therefore the voltages running across each heater path will be different slightly due to mismatch, as the rest of heater paths will run in an open-loop fashion (see FIG. 11).

In another embodiment, all heater paths are in closed loop. The benefit of doing so is to have all NMOS transistor drivers been driven by the same power voltage which is generated by the DAC. By carefully sizing the driver transistors, VDS can be set to be very small, hence the power loss on the heater drivers can be minimized.

Temperature Sensor Circuit and Temperature Control

Preferably, the chip comprises one or more temperature sensors; more preferably, the chip comprises an array of temperature sensors evenly distributed across the chip. A temperature sensor may be a PN junction in the substrate or use more complicated circuitry to implement a Proportional To Absolute Temperature sensor (each of which are known in the field of electrical engineering). The number of temperature sensors per chip is dependent on the number of heaters and ISFET sensors. In one embodiment, the ratio between temperature sensors, heaters and ISFET sensors may be 1:1:1 respectively. In a preferred embodiment, the number of temperature sensors is less than the number of ISFET sensors, which is less than the number of heaters.

Temperature sensors are positioned relative to the position of the heaters and ISFET sensors. Preferably, the temperature sensor is located away from the heater. More preferably, the temperature sensor is not located proximal to the heater, such as directly underneath a heater.

In some embodiments of the invention, the temperatures reported by the temperature sensors on chip are sent to an external microcontroller, where a PID (proportional-integral-derivative) control algorithm is implemented to control the heaters on chip in a closed loop fashion in order to achieve the target temperature(s).

Packaging of the Integrated Sequencing Chip:

The sensor chips can be packaged in a traditional IC package format on a leadframe or laminate substrate with a customized opening (e.g. a well, a chamber) to expose the chip surface for DNA sensing. The types of packages can be any main stream or customized formats, such as CLCC, PLCC, TSSOP, QFN, BGA, SOIL, etc. The choice of size, material, design of the package is depending on the application and final assembly of the sensing device.

It will be appreciated that the apparatus may comprise a thermocycler. During amplification, the temperature of the thermocycler alternates between denaturing, hybridization and annealing temperatures (T1, T2 and T3 respectively). Preferred embodiments provide this by providing sufficient power needed to achieve a range of heating ramp rate, while providing sufficient cooling fluid flow and/or fan speed to achieve a range of cooling ramp rate. Several factors affect the design of the heating and cooling speed. One of which is the resistance of the heaters, which determines the routing and layout of the heater track on the chip. Also the package design of the chip can play a role in of the ramp rate of heating and cooling.

Preferably, a polymerase for amplification is the Taq polymerase. It is also preferred that a polymerase useful for both amplification and sequencing is Bst polymerase.

Removable Seal

The removable seal, referred to herein as a sealing cap or sealing means, is suitable for sealing (containing) a reaction. It therefore provides a means of sealing (containing) the reaction and its reagents from the environment and adjacent wells. This removable seal is most preferably provided for the amplification reaction. It may also be used for the sequencing reaction (and thus either or both of the amplification and sequencing reactions), but it is most preferably used in sealing off the amplification reaction.

The removable seal may be a liquid, such as an oil, or a wax. This may be applied by a pump as described herein. It may be removed by washing, for instance with suitable solvents, as described elsewhere herein. Alternatively, the removable seal may be solid, such as a lid. This may be made of glass or other inert immaterial, for instance, or heat resistant silicone pads or thermoplastic elastomers (TPE) mentioned above. It may be applied by being located above the chip, preferably driven by a motor operated by a suitable controller to lower the seal onto the top surface of the microfluidic structure and, optionally, sensing means to detect correct location. The seal preferably comprises a compliant surface for deformably engaging the microfluidic structure. A solid removable seal may be removed by the user or by a motor as exemplified above.

With regards to the use of a removable seal at the sequencing stage, it is a preferred option. Where it is not required, there may be a continuous alternating flow of nucleotides and washes. These are preferably performed at room temperature. In some embodiments, it may be desired to increase the rate of incorporation, and hence rate of sequencing, so elevated temperatures (above room temperature, i.e. 24 degrees C.) can be used. In that instance, a removable seal may be advantageous for the sequencing step. At elevated temperatures of sequencing, it will be appreciated that solid removable seal are preferred. However, one reason for not including a removable seal is that it may decrease the rate of overall workflow. A solid removable seal for the sequencing stage may also minimize ion diffusion.

Combinations of liquid and solid removable seals are envisaged if removable seals are required for both amplification and sequencing. For instance, a liquid sealing means (removable seal) may be used for sealing off the amplification reactions, whilst a liquid or solid sealing means (removable seal) may than be used to seal off the sequencing stage.

In some embodiments, the sequencing reactions are performed at ambient (i.e. room) temperature with the fluid reagents preferably heated externally prior to delivering to the chip. This method is efficient and is also advantageous for sequencing because it provides more optimal conditions for the polymerase/reaction and also increases the rate of incorporation during sequencing.

It is also preferred, that the heating means is suitable for thermocycling. Indeed, thermocycling is a preferred method, wherein steps for denaturation, annealing and extension can be envisaged.

The amplification of the template polynucleotide occurs on a surface of said chip. It will be appreciated that this may include a number of separate surfaces. It will also be appreciated that this may be considered as occurring in, on or at a surface or surfaces. It is preferred in one embodiment that the amplification occurs within a device adjacent the chip, whereas in another preferred embodiment, this may occur in one or more (but preferably thousands or more as described elsewhere) discreet wells, for instance microwells.

In the former embodiment, the amplification of different fragments of a nucleic acid may all occur in one chamber and then flow to wells on the chip.

In the latter embodiment, it is preferred that individual fragments are amplified, each in a discreet well (such that, preferably, there is on average one template per well).

It is thus preferred that the amplification of a template and subsequent sequencing of the amplified template occurs in the same well.

It will be appreciated that the template is contained within a sample. The sample is a fluid and may include suitable buffers. As mentioned previously, nucleic acid templates in a sample may be fragmented into smaller lengths of nucleic acid templates that are amenable to in vitro amplification. In the preferred embodiment, the template is about 100-500 bp in size. Although an exact copy of the template produced by amplification is referred to as amplified template, it should be understood that there are no structural differences between a template and an amplified template, one is merely a copy of the other. The terms amplified template and amplicon are used interchangeably. The terms amplification and clonal amplification are also used interchangeably. Clonal and clonally refer to a nucleic acid population being substantially identical copies of a given template, whereby a given template is typically unique from the other templates or nucleic acid fragments.

The terms template, nucleic acid template, template nucleic acid and template polynucleotide are used interchangeably. Whilst there may be various definitions of the term template in the prior art, for the purposes of this application, it will be taken to mean a length of nucleic acid that may be copied during amplification or sequenced during sequencing. That is to say, a template is a length of nucleic acid that may be acted upon by a polymerase during the processes of amplification and sequencing. The template nucleic acid is preferably DNA or RNA and may be single or double-stranded. If double stranded, it will be appreciated that there must be at least partial separation of the strands to allow the relevant polymerase to act. Alternatively, polymerases with strand displacement activity may be used. The template is preferably single stranded. The terms target and template strand may be used interchangeably, but essentially relate to the nucleic acid to be amplified and subsequently sequenced. This nucleic acid may be just a few bases in length and the upper limit can be many orders of magnitude higher, the only limitation being spatial considerations regarding, for instance, the well size (if used) and kinetic limitations. Where a template is referred to as a species, it is taken to mean a particular or unique template from a population of many different templates. For examples, a sample of nucleic acid that has undergone fragmentation will comprise many smaller fragments of nucleic acid template or in other words, many species of nucleic acid templates. As a further example, a well may contain many nucleic acid templates of a single species, in which case there are multiple copies of one particular template.

The sequencing step determines the sequence identity of bases of the template polynucleic acid (or at least a portion of them). These may include de novo sequencing, where the prior knowledge of the template to be sequence is lacking. Alternatively, targeted sequencing or re-sequencing may be performed wherein, for example, the identity of a particular SNP is to be determined.

The chip may be considered to be 'integrated.' This is because it allows amplification and subsequent sequencing on the same chip. The heating means may also be provided as part of a base of the chip.

Figure 4:
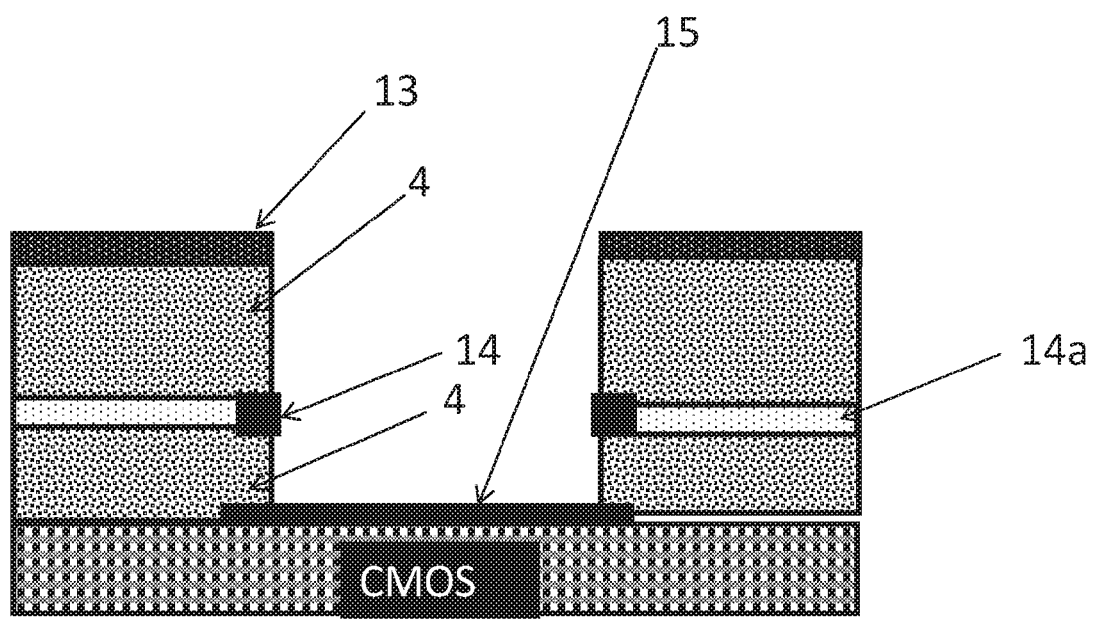
FIG. 4 is a profile view of one embodiment of a well structure

An example of a well structure of the sensing apparatus will now be described in more detail with reference to FIG. 4. A sensing layer, which is positioned above a CMOS chip, is exposed on the bottom surface of the well. A silicon dioxide well wall may be covered by a layer of TiN or Al. The layer of TiN or Al is coated with AgCl, on the surface that is exposed to the well, to form the reference electrode. The reference electrode biases the voltage potential of the fluid above the sensing layer to set the operating point of the ISFET such that changes in the fluid potential due to the release of protons in the fluid can be measured. It is preferable that the layer of TiN or Al is positioned sufficiently low in the well such that the reference electrode is submerged when the well contains a reaction mixture. It is preferable, as is shown in the embodiment, that the top surfaces of the well walls are covered with a layer of hydrophobic material. Suitable hydrophobic materials include but are not limited to Organic polymeric or inorganic or nanomaterial e.g. PMMA, PE, PP, Su-8 or photo resist material, parylene or it can be superhydrophobic TiO2 naoparticle coating. The hydrophobic material helps to break the surface tension of the fluid between wells during the sealing process thus removing micro voids which may form and lead to cross contamination or evaporation of the fluid from the well. Sealing of the wells will be discussed in more detail below.

Figure 5:
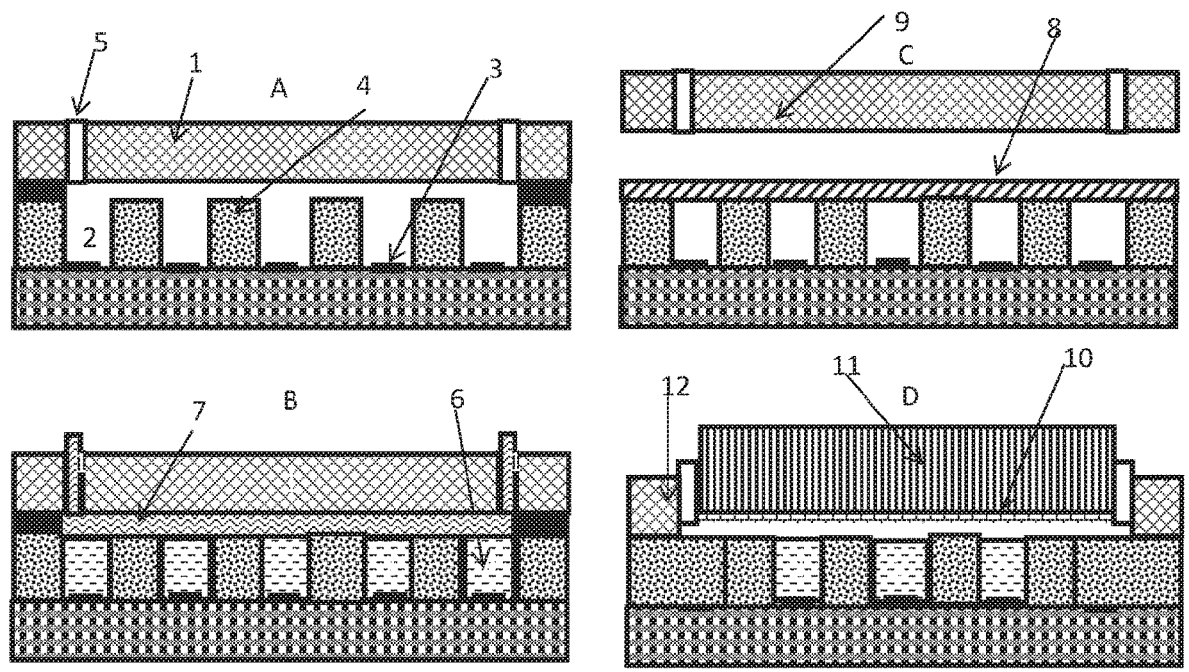
FIG. 5 is a schematic of different embodiments of a removable seal.

Embodiments of the removable seals, as shown in FIG. 5, will now be described in further detail. A flow cell is included in each of the embodiments shown in FIG. 5. The flow cell may be integrated with the sensing apparatus as a single unit (for example embodiments A, B and D) or it may form a separate detached component (for example embodiment C).

Embodiment A of FIG. 5 shows a sensing apparatus with an integrated flow cell 1. The flow cell comprises fluidic valves 5, providing an inlet and an outlet through which fluid may be flowed into and out of the wells. Each well comprises a sensing layer 3. The well walls 2 may be made of SiO2. The wells of embodiment A are not sealed.

Embodiment B shows the sensing apparatus of embodiment A, wherein the wells containing amplification reactions 6 are sealed with a removable liquid seal 7. The liquid seal is preferably an oil, for example a mineral oil and more preferably paraffin oil or silicone oil. The removable liquid seal may be introduced into the sensing apparatus via the flow cell by means of a pump or a pressure source and one or more controllable valves that control entry of reagents. An example of such pump/pressure source and control valves is described in U.S. Pat. No. 7,948,015B2 and US2010/0301398A1, hereby incorporated by reference.

Where oil is used as a removable seal, the oil can be removed by several rounds of alternating washes of organic solvent and pre-sequencing buffer containing suitable detergents these detergents can be any of non-ionic or a mix of non-ionic and anionic or cationic type or it may be silicone based detergents. Alcohols such as methanol, isopropanol, ethanol, isobutanol are suitable organic solvents. Others such as diethyl ether can also be used. Examples of organic solvents for removing mineral oil can be found in U.S. Pat. No. 7,842,457B2, hereby incorporated by reference.

Embodiment C shows a sensing apparatus and a detached flow cell that is lifted to an open position. The wells of embodiment C have been sealed using a pressure sensitive adhesive (PSA) 8. PSA forms bonds between the adhesive and an adherend (in this case the top surface of the well walls) on application of light pressure. The properties of PSAs are well known in the art. A layer of PSA is applied on top of the wells such that contact is made between the PSA and the top surface of the well walls. Pressure is applied to the PSA such that adhesive bonds are formed between the PSA and the top surface of the well walls. Pressure may be applied by any form of external pressure, for example through the use of a roller or lowering of a clamp coupled to a mechanical actuator. Pressure may also be applied by lowering the flow cell 9 onto the sensing apparatus to a closed position. This may be done using a mechanical actuator.

It is preferable that the adhesive strength of the PSA is sufficiently low such that the PSA can be readily removed as required. It is preferable that the adhesive strength of the PSA is between 0.1-10 N/cm$^2$. It is more preferable that the adhesive strength is between 0.1-5 N/cm$^2$.

Embodiment D shows a sensing apparatus with an integrated flow cell 12 comprising a flexible non-sticky membrane 10 between the fluidic inlet and outlet valves of the flow cell. The membrane is preferably a heat resistant silicone pad or a thermoplastic elastomer. A block material coupled to a mechanical actuator may be lowered to apply a uniform pressure on the membrane. This will cause the membrane to push against the top surfaces of the microfluidic wells so as to seal the wells. To remove the seal, the block material is lifted away from the membrane, causing the membrane to return to its original position, raised above the wells.

Biological and Chemical Reactions

It will be appreciated that, in some embodiments, the reagents used in the processes of amplification and sequencing do not form a physical part of the apparatus, the exception being any oligonucleotides that are immobilised in the wells or beads prior to amplification.

In other embodiments, these reagents may form part of the apparatus (as they could, for instance be provided in a housing) or, together with the apparatus, form a kit. As such, the invention also provides a kit comprising the apparatus and reagents for amplification and sequencing of the template and, optionally, beads as described herein.

The volume of a microfluidic device may range from 1 pl to 10 µl or greater than 10 µl. The heating means can, in one embodiment, allow the amplification reaction to take place within the microfluidic device where both the optimal temperature and condition can be achieved for both thermocycling and isothermal amplification reactions, as well as hybridization of primers or oligonucleotides.

It will be appreciated that nucleic acid templates in a sample will need to be prepared before they are exposed to the sensing apparatus for amplification and sequencing. Steps for preparation of a sample may include, but is not limited to, lysis of cells, purification of nucleic acid material (e.g. DNA), pre-amplification of a desired region, amplicon purification, fragmentation of the amplicons (e.g. by sonication, nebulisation or by using restriction enzymes), end repairing of the fragmentations and universal adaptor attachment via ligation. All the individual steps are well known in the art as is the combination of the individual steps for the process of preparing nucleic acid samples for amplification or sequencing.

In one embodiment, the well of the ion sensitive apparatus contains immobilized oligonucleotides or chemical group that bind to the nucleic acid template. The oligonucleotides or chemical group can be immobilized on a solid support such as a bead and/or on the wall(s) of the well. The immobilized oligonucleotides or chemical groups act as 'capture sites' for the nucleic acid templates. A capture site denotes an oligonucleotide immobilised on a solid support which is able to bind to (i.e. hybridise) or 'capture' a nucleic acid template.

The oligonucleotides may be attached to the solid support (e.g., beads or walls of the well) via chemical groups that are bound to the surface of the support. The attachment of the nucleic acid to the bead can be performed by means known in the art. For example, covalent chemical attachment of nucleic acid to the beads can be accomplished using standard coupling agents such as water soluble carbodiimide, which can be used to link the 5'-phosphate of a DNA sequence to amine-coated beads through a phosphoamidate bond. Alternatively, specific oligonucleotides can be coupled to the bead using similar chemistry.

Oligonucleotides may be immobilised on the well walls via a process of silanisation, activation and coupling. Silanisation of the well walls ($SiO_2$) can be performed by induced hydrolysis of $SiO_2$. Silanisation can be achieved by using silanes such as (3-glycidyl oxy propyl) trimethoxysilane (3-GPS), (3-Amino propyl) triethoxysilane, aminophenyl trimethoxysilane, (3-mercaptopropyl) trimethoxysilane (3-MPTS) or haloacetamido silanes. It is preferable that silanisation is restricted to $SiO_2$ surfaces only and not the sensing layer to avoid any complexities regarding ISFET performance.

Silanised surfaces of the wells may be activated by reacting with one of, but not limited to, dithiobispyridine, N-hydroxy succinimide (NHS), EDC or other carbodimides. It is preferable that activation is by a compound that has a low buffering capacity so as not to absorb protons released during the reactions.

The oligonucleotides may then be coupled to the surface. Oligonucleotides readily react with the activated silanised surface to become immobilised on the surface of the wells. Prior to immobilisation, the oligonucleotides may be 5' modified with a functional group such as amine, -thiol, acrydite, carboxy, hyroxy, azide or even biotinylated.

More detail on the process of silanisation of a solid surface may be found in the following references:

1, Bhatia, S. K.; Shriver-Lake, L. C.; Prior, K. J.; Georger, J. H.; Calvert, J. M.; Bredehorst, R.; Ligler, F. S. Anal. Biochem. 1989, 178, 408-413.
2, Lee, Y. W.; Reed-Mundell, J.; Sukenik, C. N.; Zull, J. E. Langmuir 1993, 9, 3009-3014.
3, Shriver-Lake, L. C. In Immobilized Biomolecules in Analysis; Cass,
4, Kallury, K. M. R.; Krull, U. J.; Thompson, M. Anal. Chem. 1988, 60, 169-172.
5, Lyubchenko, Y. L.; Blankenship, R. E.; Gall, A. A.; Lindsay, S. M.; Thiemann, O.; Simpson, L.; Shlyakhtenko, L. S. Scanning Microsc. Suppl. 1996, 10, 97-107.
6, Vandenberg, E.; Elwing, H.; Askendal, A.; Lundstrom, I. J. Colloid Interface Sci. 1991, 147 (1), 103-118.
7, Leyden, E. D. Silanes, Surfaces and Interfaces; Gordon and Breach: New York, 1986.

The density of the oligonucleotides attached to the well walls can be in the region of 1 micro Molar to 1 pico Molar per $cm^2$. The density achieved is largely dependent on the salinisation process. The density of oligonucleotides may be increased by further reacting the silanised well walls with dendrimeric molecules or hyperbranched polymers which can provide further functionalised silanised surfaces.

It is preferable that the sensitive Ag/AgCl layer of the reference electrode is protected during the process of oligonucleotide immobilisation described above. This may be by covering the Ag/AgCl of the electrode with a protective layer such as wax, which can be removed prior to use of the apparatus during the sequencing process.

The template to be amplified and sequenced ideally will be ssDNA or RNA, however, double stranded DNA may be envisaged wherein it contains "sticky ends" resulted from, e.g. restriction enzyme digested. The orientation-specific sticky end will hybridize to the oligonucleotide immobilized on beads or solid support and ligase can be added to form covalent bond between template and the oligonucleotide.

The template may be attached to the solid support before amplification, or it may be attached during amplification.

The Nucleic acid templates can be DNA or RNA such as, but not limited to, purified genomic DNA (which generally includes cDNA) or mRNA. The nucleic acid templates may be naturally or non-naturally occurring and may be obtained from various sources such as, but not limited to, bodily fluid or tissues, bacteria, virus, or cDNA library. For RNA, an initial step of reverse transcribing the RNA to DNA prior to amplification is preferred.

For de novo sequencing, the nucleic acid template may be prepared using standard sample preparation/DNA library construction method known in the art (e.g. NEBNext Fast DNA library Prep Set 4 from New England biolabs). Briefly, the nucleic acid is fragmented, end repaired, universal adaptor ligated and cleaned up with optional pre-amplification of 4-8 cycles. For gene specific amplification and sequencing, which may contain particular mutations or SNP, nucleic acid may be fragmented followed by clean up. For both de novo and gene specific sequencing, specific fragment size may be enriched.

The fragmented nucleic acid templates are mixed with amplification reagents comprising dNTPs, polymerase, and first and second primers that have complementary sequence to the 5' and 3' region of the template of interest and each may contain a unique universal adaptor sequence. The mixture is added to the wells (for illustrative purpose) at a limiting dilution such that each well contains on average only a single copy of a template. The fragmented nucleic acid templates may be delivered into the wells by methods such as liquid flow such that each well contains on average only a single copy of a template. Methods for obtaining a single copy of a template in each well will be described in further detail later.

The templates may be clonally amplified using thermal cycling (e.g. by various polymerase chain reactions (PCRs) that use thermal cycling) or isothermal amplification method (e.g. rolling circle, strand displacement amplification (SDA)).

For PCR, amplification is performed with greater than 10 cycles, 20 cycles, 30 cycles or 40 cycles using optimal buffered condition depending on the application and level of analysis desired. For example, targeted sequence analysis such as that for genotyping, identifying SNPs, or simpler sequencing applications may require fewer cycles.

For amplification taking place in the wells, immobilized oligonucleotides will be provided in the well to bind amplicons. During the denaturing stage of a PCR, double stranded amplicons are separated to form single stranded DNA; thus upon the annealing stage, a portion of the single stranded DNA will hybridize to the immobilized oligonucleotides in a strand specific manner. In one embodiment, the ratio of first and second primers may be altered to bias production of strand specific single stranded DNA (ssDNA), thus increased the probability of ssDNA hybridizing to the immobilized oligonucleotides (e.g. if second primer specific ssDNA is preferred, the ratio of first to second primer may be set to greater than 1:1, 1:4, 1:8 or greater than 1:50).

The immobilized oligonucleotide may then act as a primer to extend the nucleic acid using hybridized ssDNA as template. Repeated rounds of denaturation, annealing and extension are used to (clonally) increase the copy number of the template in the well, and these copies are immobilized on solid supports, i.e. surfaces situated in the well.

In one embodiment, the quantity of amplified template can be monitored by ISFET sensor(s) which detects the accumulation of protons in the well.

It is preferred that once a desirable amount of clonally amplified template is achieved, the sealing cap is removed. The wells are then preferably washed to remove reagents such as buffer compounds, primers, dNTPs, polymerases, protons and nucleic acid templates that are not immobilized to the solid support.

Immobilized single stranded DNAs are used as preferred (amplified) templates for subsequent sequencing reaction. Therefore, to ensure only ssDNAs remain immobilized on solid support, the wells are washed with, for example, an alkaline solution to denature the template (strand separation).

In a preferred method, sequencing is imitated by hybridising a sequencing primer to the 3' region of the immobilized single-stranded nucleic acid (in this example, ssDNA) template, and a sequencing polymerase (such as Bst polymerase or another thermal stable polymerase) then binds to the sequencing primer/-stranded nucleic acid (ssDNA) template complex.

This is followed by addition of nucleotides, principally deoxynucleotides, wherein each nucleotide (e.g. dATP, dGTP, dCTP and dTTP) is introduced into the wells separately (i.e. in separate 'waves'). If a complementary base exists in a template in a particular well, then the nucleotide will be hydrolysed by the polymerase (in this example, Bst) and incorporated extending from the 3' of sequencing primer. Incorporation of nucleotides will lead to the production of a proton as a by-product, which is detected by the ISFET sensor(s) and signalling a positive response. On the other hand, lack of incorporation of nucleotide(s) will not generate proton(s) and thus no signal will be produced. Through repetition of the process of adding one nucleotide at a time, wherein addition of each nucleotide is followed by a flow of washing buffer containing no nucleotide, the complete sequence is delineated.

As such, progressive waves of single nucleotides, each wave followed by a step to remove all unbound nucleotides (a 'clearing step'), such as a wash, are preferred. The signal form each ISFET is collated and, ultimately, the sequence of the amplified template in each well is determined. In turn, the results from each well can be analysed and overlapping portions matched to provide up to a whole genome, if relevant.

The methods of detecting pH changes with ion sensitive apparatus for DNA sequencing are described in the art and incorporated herein by reference (see, e.g., Patent Application Nos. U.S. Pat. Nos. 811,459; 7,686,929; 7,888,015; EP2129792; WO06/005967; US2010/0255595; and GB1112140.7; Rothberg J M et. al., Nature 475:348-52 (2011)). Another publication by Rothberg is US2010/137143. Our own publications include WO 2008/07014 and WO2003/073088.

In various embodiments, the sequence of the oligonucleotides immobilized on solid support has sequence complementary to 5' or 3' of the nucleic acid template. Preferably, the oligonucleotide has sequence identical to all or a portion of first or second primer used for clonal amplification, preferably identical to either the universal adaptor sequence of the first and second primers. In a preferred embodiment, the oligonucleotides are conjugated at the 5' end to biotin and each well contain one or more Streptavidin bead(s) bound to biotin-conjugated oligonucleotides comprising of a universal adaptor sequence. Alternatively, universal adaptor oligonucleotides may be conjugated to the surface within the wells. Other covalent attachment of oligonucleotides onto modified surface may be used (e.g. UV crosslink on unmodified glass SiO2).

The first and second primers may only contain sequence complementary to the universal adaptor, but may additionally contain sequence complementary to the target gene of interest.

In particularly embodiments where an oil (preferably a mineral oil) is used as a removable seal, also referred to herein as a sealing cap, the oil can be removed by several rounds of alternating washes of organic solvent and pre-sequencing buffer. Alcohols such as methanol, isopropanol, ethanol, are suitable organic solvents. Preferably isobutanol is used.

In one preferred embodiment, single copies of single stranded nucleic acid templates are first hybridised to beads containing oligonucleotides, and are then introduced into wells with amplification reagents and primers. Preferably, the initial templates are then clonally amplified in the well. The net result is a clonally amplified population of complementary strands captured on the beads.

A reference ISFET may be provided within the apparatus. To this end, there may be control wells or otherwise empty wells. Empty wells may arise for a number of reasons, either they may be left purposefully empty or designed to avoid immobilisation. Furthermore, if on average only 1 template per well is used, and a large number of wells are provided on the chip, then there should also be some wells that will have no template immobilised therein to sequence (and optionally amplify prior to sequencing).

It is preferred that the sequencing polymerase, preferably Bst, and the nucleic acids are incubated in the wells.

The nucleic acid templates can preferably be distributed by flowing or spotting the sample into each well. To ensure on average only single nucleic acid template is achieved per well, the sample can be diluted. UV can be used to degrade nucleic acid template that are not proximate to the sensor i.e. are visible above the top of the well (when viewed along the plane of a flat chip comprising wells. This is particularly useful for degrading dsDNA which will not anneal (with the oligonucleotide for immobilisation) within the well until denatured to provide ssDNA.

Thus, this UV or equivalent serves as an alternative to a washing step to clear away DNA not in a well or any dsDNA not in a well.

The template to be amplified is most preferably dsDNA. For sequencing the sequencing stage, the template will preferably be in ssDNA form. Strand separation, melting and or denaturation, as appropriate for amplification or sequencing, is envisaged if double-stranded DNA or RNA are provided.

The oligonucleotide referred to herein is an oligonucleotide for immobilisation within a well or on a surface of the chip. This is a linker to distinguish it from the primer or probe (at least one of which needs to be immobilised at one end to prevent the amplification or sequencing complex from washing away).

If there is no sealing cap present (including if one has been removed), then there is or can be a constant flow of liquid into or out of the wells.

Solid-phase amplification such as bridge amplification is preferred as it allows an immobilized template to be amplified using adjacent primers to form an immobilized cluster of clonally amplified templates. Bridge amplification usually contains at least two populations of oligonucleotides immobilized (e.g. on the walls of the wells or the surface of the beads situated) in the well. For example, the first and second oligonucleotides may be designed to hybridize to the 5' and 3' of the template respectively. The method involves introducing on average one template into each well, where for example the 5' of the template is hybridized to the first oligonucleotide and the 3' of the template hybridize to the second oligonucleotide, forming a bridge. In the presence of nucleotides and polymerase, nucleic acid extension proceeds from the 3' end of the second oligonucleotide. Repeat rounds of denaturation, hybridization and extension leads to a cluster of amplified template.

In general, however, no sealing caps (removable seals) are required for solid-phase amplification since all clonally amplified templates are immobilized, and there will be a constant flow of reagents over the wells.

The amplification and sequencing reactions of a nucleic acid template are preferably performed in the same well.

In a preferred embodiment, the semiconductor chip and microfluidic structure are disposable. An advantage of having a disposable sensing apparatus is maximising accuracy of sequencing by eliminating any possibility of cross contamination between uses. A further advantage is the ability to provide a means for temporarily obscuring or sequestering oligonucleotides immobilised on a surface in a well, which would otherwise not be possible if the sensing apparatus was not disposable. Such means for temporarily obscuring oligonucleotides immobilised on surface in a well is described in further detail below, but may include a wax layer on the surface of the well.

Embodiments of Uses of the Sensing Apparatus

For effective sequencing, it is desirable that the sequencing reaction in each well contains only one species of nucleic acid template. As amplified templates (amplicons) are used for sequencing, it is desirable that each clonal amplification reaction is initiated with a single nucleic acid template.

Limited Dilution Approach

In this particular embodiment, each well of the sensing apparatus is modified with a plurality of universal primers and the number of templates provided are restricted. That is to say, universal primers have been immobilised to the surface of the well walls and/or to the surface of bead(s) which is contained in the well. The templates have been prepared for amplification and sequencing as described previously, including the step of end ligating universal adaptors to the templates.

When a sample is flowed into the wells, the nucleic acid templates bind to the wells by hybridisation between the universal adaptors and universal primers.

The resulting population of wells may be divided into three categories: wells containing no nucleic acid template; wells containing one nucleic acid template; and wells containing 2 or more nucleic acid templates. The distribution of these categories can be modelled by the Poisson distribution. The expected distribution of the different categories of wells is dependent on the ratio of the number of templates to the number of wells. Where there are more templates than wells, the distribution will be biased towards wells with 2 or more nucleic acid templates. Where there are more wells than templates, the distribution is biased towards wells that contain no template.

Based on the Poisson distribution model, it has been calculated that the optimal ratio between the number of templates provided to the wells (template copy count) and the number of wells is 1:1. At this optimal ratio, the number of wells with only a single template comprises 37% of the total number of wells. This ratio may be between 2:5 and 2:1, such that the percent of wells with a single copy is still about 25%. The ratio may be adjusted by adjusting the number of templates in a sample either by concentrating up or diluting down.

It should be noted that the change in the ratio is not directly proportional to the change in the bias of the distribution. As such, a significant change in the ratio is necessary to see a small change bias in the distribution. Consequently, it is only necessary to ascertain a rough estimate of a template copy count in a sample to obtain optimal distribution bias.

In a given sample, the template copy count will fall within an expected range. This range is known as the natural sample variability. In cases where the template copy count is considered to fall outside the acceptable variation, there are methods to ascertain, or 'control' the template copy count. One such method is to carry out an additional amplification step, prior to amplification and sequencing, wherein the concentration of a reagent (e.g. primers) is a limiting factor. Therefore, after this additional amplification step, the nucleic acid template copy count can be set to a predetermined amount based on the concentration of the limiting reagent.

Another method for controlling template copy count is to add a known number of capture sites, e.g. on a bead, to the sample and subsequently wash away the excess nucleic acid templates. The templates bound to the beads may then be released in solution to obtain a predetermined amount.

Once the nucleic acid templates have hybridised within the wells, any unhybridised templates are removed by a washing step. The wells are then filled with an amplification reaction mixture. Reagents required for PCR or other amplification techniques are well known in the art and have been mentioned previously. Once the reaction mixture is in the wells, the wells are sealed with a removable seal. The amplification reaction then takes place in the sealed well, the seal preventing any cross contamination of templates between wells. During amplification, the amplified templates hybridise to the immobilised universal primers and are therefore anchored to the wells. Once the amplification reaction is finished, the seal is removed and the wells are washed to remove any unbound templates. The templates may optionally undergo a denaturation step to ensure that all the templates for the sequencing reaction are single stranded. Where a denaturation step is applied, an extra washing step is also required to remove any reagents involved in the denaturation step.

With the amplified templates now ready for sequencing, DNA polymerase is flowed into the cells and allowed to bind to the templates. Rounds of individual nucleotides are then flowed over the wells, with a washing step between each nucleotide round. The ISFET detects whether there is a change in pH with each round of nucleotides that are flowed into the wells, a change in pH signalling an insertion of a nucleotide to a nascent strand. The sequence of the template obtained from each well is then compiled to generate the sequence of the original nucleic template in a sample.

It is possible to distinguish the sequencing result from wells with no template or wells with two or more templates, and therefore, discard these as necessary, either during real-time data processing or post-processing. Wells with no template bound to it will have had no template amplified and so there will have been no amplified templates. As such, no sequencing result will be obtained from these wells. Wells with 2 or more templates will have had copies two or more species of amplified templates after the amplification step. As such, during sequencing, these wells are likely to provide an indication of insertion reactions for a greater number of rounds of nucleotides than expected. Moreover, in these wells, the changes in pH for each insertion reaction will be weaker compared to wells with one species of amplified templates.

Single Capture Site

In another embodiment, the distribution of unique templates may be improved by controlling the number of capture sites (i.e. immobilised oligonucleotides) in a well. In this case, the templates are provided well in excess of the number of well/binding sites. By limiting the number of capture sites to one per well it is possible to ensure that every well will only have a single template bound therewithin. The capture site is an immobilised oligonucleotide, preferably a universal primer.

In one embodiment, in each well, there is a single bead comprising a single immobilised oligonucleotide. This may be achieved by using a capture bead that is sufficiently large relative to the well, such that each well can only hold a single capture bead.

Alternatively a surface of the well may be arranged to hold only a single bead. For example, the size of an area on the surface having a complexing agent specific to the bead material may only accommodate a single capture bead. The bead may comprise Alizarin and an area on the well surface may be aluminium, formed by depositing aluminium or etching the well surface down to an aluminium layer. As a second example, an electrode (preferably the reference electrode) may be charged to attract a bead (which may be conversely charged), the area of the electrode being only sufficient to accommodate a single capture bead.

Where the wells have been provided with oligonucleotides, preferably universal primers) already immobilised on the surface of the well, the oligonucleotides will need to be sequestered from the templates in a sample such that they are unavailable for hybridisation when the template is flowed over the wells. Instead, the only capture site available in the well will be that on the bead. The oligonucleotides may be sequestered by coating the inner surface of the wells with a material that can be readily removed, such as wax.

In general, the wax may be replaced with an inactivated protein.

In a preferred embodiment, the wells of the sensing apparatus may be supplied with a wax coating or layer on the inner surface of the wells. The wax may be paraffin. A single bead will then be added to each well by methods well known in the art and previously described. The oligonucleotides or capture sites are only temporarily sequestered as they will need to be available for hybridisation with the amplified templates produced during amplification. The wax coating (which may also be referred to as a layer) will be of sufficient depth to obscure the oligonucleotides. At the same time, the well should not be filled with the wax coating or layer as this would obviate the wells. Suitable thicknesses for the wax coating or layer may be in the region of 10 nm to 100 nm. The wax coating may be applied by evaporation or, inkjet dispenser or by flowing the wax solution over the microfluidic structure.

Alternatively, the multiple capture sites may be made unavailable initially by a reversible terminator or other known techniques for blocking hybridisation or amplification, which is then removed when the unbound template has been removed. Or it may be that the single binding site has a different binding chemistry than the extra binding sites (known), meaning that only the single site is suitable for capturing the initial copy, whereas the other sites are suitable for capturing amplicons.

Where the wells of the sensing apparatus are provided without oligonucleotides immobilised on the surface of the well walls, it is not necessary for the inner well walls to be coated with wax. Instead additional sites for the amplified templates may be supplied on amplification beads, which are preferably small enough to fit around the capture bead in a well and provide a high surface area to volume ratio. The capture bead refers to the bead to which a single template has bound, being restricted to one per well. The 'amplification' beads may be supplied to each well after hybridisation of the template to the capture bead and after removal of any unbound templates via a washing step. The 'amplification' beads may be 10 nm to 100 nm.

The nucleic acid templates in the sample will have been prepared for amplification and sequencing as described previously, preferably including the step of end ligating the templates with universal adaptors.

The templates are flowed over the wells such that a single template is bound to a single bead in each well. Any unbound, excess templates are removed via a washing step. In a preferred embodiment, the wax coating is then melted by the application of heat, preferably produced by the heating means of the sensing apparatus, and optionally the wax is removed from the wells via a washing step. The wax coating may be left to melt as a consequence of the heating of the wells during the amplification process.

The wells are filled with an amplification reaction mixture containing the necessary reagents for an amplification reaction. Once the reaction mixture is in the wells, the wells are sealed with a removable seal.

The amplification reaction then takes place in the sealed well, the removable seal preventing any cross contamination of templates between wells. During amplification, the amplified templates hybridise to the immobilised oligonucleotides (preferably universal primers) and are therefore anchored to the wells. Once the amplification reaction has finished, the seal is removed and the wells are washed to remove the reagents and any unbound templates. The templates may optionally undergo a denaturation step to ensure that all the templates for the sequencing reaction are single stranded. Where a denaturation step is applied, an extra washing step is also required to remove any reagents involved in the denaturation step.

With the amplified templates now ready for sequencing, DNA polymerase is flowed into the wells and allowed to bind to the templates. Rounds of individual nucleotides are then flowed over the wells, with a washing step between each nucleotide. The ISFET detects any changes in pH with each round of nucleotides that are flowed into the wells, a change in pH signalling an insertion of a nucleotide to a nascent strand. The sequence of the template obtained from each well is then compiled to generate the sequence of the original nucleic template in a sample.

In another embodiment, the chip is provided with a single capture bead in each well. The 'amplification' beads may be provided separate to the chip, as part of a kit.

In yet a further embodiment, it may also be possible to make sure that only a single template is bound to in a well by adding a FET in each well, in addition to the ISFET. The FET will function to measure a binding charge. A positive charge is applied locally in the well using the reference electrode in each well. The electrodes may be controlled individually. The positive charge attracts the negatively charged templates from solution above the well into the well. On binding of the first template to the immobilised oligonucleotide (universal primer), the binding charge is detected by the FET. A controller monitoring the FET output signal may switch off the electrode potential from the reference electrode to prevent further templates from being attracted towards the wells. The FET may be an ISFET or there can be another transistor in the well which preferably measures the charge of the DNA which binds to the FET surface. The FET surface may contain the immobilised universal primers but in a limited number and when the template hybridizes to these primers the FET detects the charge of a single molecule and that FET can trigger the ISFET reference voltage to switch off in that particular well. Thus the single copy of template can be created for the preparation of clonal amplification step.

Once all of the individual wells have a single template bound to it, any unbound, excess templates are removed via a washing step. The wells are then filled with an amplification reaction mixture containing the necessary reagents. The wells are sealed then with a removable seal.

The amplification reaction then takes place in the sealed well, the removable seal preventing any cross contamination of templates between wells. During amplification, the amplified templates hybridise to the immobilised oligonucleotides (preferably universal primers) and are therefore anchored to the wells. Once the amplification reaction has finished, the seal is removed and the wells are washed to remove any unbound templates and also reagents used for amplification. The templates may optionally undergo a denaturation step to ensure that all the templates for the sequencing reaction are single stranded. Where a denaturation step is applied, an extra washing step is also required to remove any reagents involved in the denaturation step.

With the amplified templates now ready for sequencing, the sequencing primers hybridised along with the binding of DNA polymerase on the template. Rounds of individual nucleotides are then flowed over the wells, with a washing step between each nucleotide. The ISFET detects any changes in pH with each round of nucleotides that are flowed into the wells, a change in pH signalling an insertion of a nucleotide to a nascent strand. The sequence of the template obtained from each well is then compiled to generate the sequence of the original nucleic template in a sample.

Sequence Specific Capture

In yet another embodiment, the distribution of templates may be improved by using capture sites (i.e. immobilised oligonucleotides) that are specific to a defined sequence, which is anticipated to be, but may not be, present only in a sub-group (i.e. certain proportion) of templates. Such specific capture site are in contrast to universal primers, as used in the previous embodiments described above, which bind indiscriminately to all species of template in a given sample (via the hybridisation between universal primers and universal adaptors). Examples include primers specific to 16 SrRNA or 23 SrRNA fingerprint region of a bacteria. Primers in the wells complementary to the conserved regions within these fingerprint regions will selectively bind template from bacteria, although not all bound templates will necessarily be identical or copies Alternatively, the primers may be specific to labels added to individual starting template, in which case a monoclonal population is created within the well by capturing only amplicons which originated from that single starting fragment. Preparation of samples for use in this embodiment may not require that the templates are end ligated with universal primers. The templates may be ligated with a specific adaptor, called a 'barcode' Barcodes may be included in the sample preparation by various known means, including ligation or by simply including the barcode sequence in the amplification primers. The barcode, by labelling the amplicon's initial starting species, ensures that amplicons self-sort into monoclonal clusters on the ISFET.

By restricting each well to contain oligonucleotides for a specific sequence, it is possible to ensure that only templates comprising the defined sequence will bind to each well, thereby removing the risk of cross contamination of templates between wells. Therefore, a removable seal may not be required during amplification.

Although each well will have a specific primer, a plurality of wells may be grouped into regions, each region of wells having a particular type of primer (such as bacteria primers or virus primers), such that a single chip may contain many different sequence specific primers'. The primers in a given region may thus all be complementary to the barcode or conserved region, and each well in that region will additionally be complementary to a different target base or target sequence to detect a variant. Thus reaction activity in a given region of the chip may indicate the general presence of a bacteria genus and subsequent sequencing may determine the species of bacteria or allele variant of a species.

In either above embodiment, the templates may be amplified outside of the wells to create several mixed populations of amplified templates.

The amplified templates are flowed into the wells to allow hybridisation of the templates within the wells. Only templates comprising a defined sequence complimentary to the sequence specific primers will bind to the wells. After hybridisation of the templates within the wells, any unhybridised templates are removed by a washing step. The wells are then optionally filled with an amplification reaction mixture containing the necessary reagents to increase the signal strength. Reagents required for amplification are well known in the art and have been mentioned previously.

During the optional amplification step, the amplified templates hybridise to the immobilised oligonucleotides ('primers) and are anchored to the wells. The wells are washed to remove the reagents of the amplification reaction and any unbound templates. The templates may optionally undergo a denaturation step to ensure that all the templates for the sequencing reaction are single stranded. Where a denaturation step is applied, an extra washing step is also required to remove any reagents involved in the denaturation step.

With the templates now ready for sequencing, DNA polymerase is flowed into the wells and allowed to bind to the templates. Rounds of individual nucleotides are then flowed over the wells, with a washing step between each nucleotide. The ISFET detects any changes in pH with each round of nucleotides that are flowed into the wells, a change in pH signalling an insertion of a nucleotide to a nascent strand. The sequence of the template obtained from each well is then compiled to generate the sequence of the original nucleic template in a sample.

The following represents a very particular embodiment of the invention and, although preferred, is provided mainly for exemplification purposes. It relates to an embodiment where amplification occurs in the well, but it can equally be applied to where amplification occurs elsewhere:

1) Sample comprising nucleic acid of interest (the template) is taken and sample prepared, preferably fragmented;
2) Prepared sample added to multiple (at least 2, but likely 1000's or millions) of wells, the wells comprising primers suitable for amplification of the template;
3) The well also comprises polymerase and a source of nucleotides (e.g. dNTPs)—these can be added with the template or can be present already;
4) The wells may optionally comprise one or more beads, but at least one of the primers must be immobilised (either directly or indirectly) via an oligonucleotide on a surface within the well (either the inner surface of the well or chamber, or on a bead if present);
5) Amplification of the template occurs at 60-65 degrees C. for isothermal amplification or at suitable temperatures for PCR;
6) Once a sufficient level of amplification is achieved (which may be determined by a number of means, including simple cycle number or time, preferably by the ISFET as in our earlier qPCR publication), depending on the required signal strength, the amplification reagents and any un-bound (i.e. not immobilised) template are cleared out by washing, leaving immobilised template;
7) Waves of individual dNTPs are passed over or into the wells and each ISFET detects whether there is proton release at that well corresponding to each wave, so that proton release (and hence nucleotide insertion) is correlated with the sequence of the growing (nascent) strand based on the immobilised strand, thus providing the sequence of the immobilised strand (via its compliment, the nascent strand to which the dNTPs are being added by the polymerase);
8) Collation of ISFET data occurs and sequence is determined.

Also provided is a method of amplifying a nucleic acid template followed by sequencing of the amplified template, the method comprises the steps of:
A) combining nucleic acid template with amplification reagents comprising of polymerase, dNTPs and primers for nucleic acid amplification to form a mixture;
B) providing the mixture in A) to a plurality of wells in an ion sensitive apparatus wherein the ion sensitive apparatus comprises of ISFET sensor, heater and temperature control, and wherein each of the wells is in contact with at least one ISFET sensor;
C) performing nucleic acid amplification in the wells;
D) identifying the sequence of the amplified template in the wells.

The invention also provides a method of amplifying a nucleic acid template followed by sequencing of the amplified template, wherein both the amplification and sequencing are performed in the same well on a chip, the method comprises the steps of:
A) Mixing the nucleic acid template with amplification reagents comprising polymerase, dNTPs and first and second primers, wherein the first primer is capable of binding to a first of single stranded nucleic acid template species, and the second primer is capable of binding to a second of single stranded nucleic acid template, wherein the second of single stranded nucleic acid template species is complementary to the first;
B) contacting the mixture in A) with a plurality of wells on an ion sensitive apparatus such that each well comprises on average one single copy of the nucleic acid template, wherein each well comprises oligonucleotides immobilized on a solid support surface and wherein the sequence of the oligonucleotide is identical to at least a portion of the first primer, wherein the oligonucleotide is capable of binding to the first of single stranded nucleic acid template species;
C) covering the well with a sealing cap;
D) performing nucleic acid amplification reaction whereby the nucleic acid template is amplified with first and second primers, and wherein the first of single stranded nucleic acid template species are preferentially generated and are capable of binding to first primers and oligonucleotides immobilized on solid support;
E) extending the oligonucleotides to form the second of single stranded nucleic acid template species, wherein the sequence of second of single stranded nucleic acid template species is complementary to the first of single stranded nucleic acid template species hybridized to the oligonucleotides;
F) removing the sealing cap from C);
G) denaturing the immobilized nucleic acid template wherein only the second of single stranded nucleic acid template species bound to the solid support;

H) adding sequencing primer and polymerase to the well, wherein the sequencing primer hybridize to a 3' region of the second of single stranded nucleic acid template species;
I) adding one nucleotide to the well;
J) detecting a change of pH resulting from proton release if the nucleotide is hydrolysed and incorporated;
K) washing the wells to remove unincorporated nucleotides;
L) repeat I-K to delineate the sequence of the nucleic acid template.

Preferably, the apparatus comprises an ISFET sensor, heater and temperature control, and wherein each well is in contact with at least one ISFET sensor.

It should be appreciated that in the above discussion several steps have been disclosed and the skilled person will appreciate that these steps may be combined and some steps omitted as appropriate to provide a method or apparatus that creates or assembles a population of templates (which is at least identical on a region of interest), which templates are immobilised within a well. The order of these steps may be changed and the extent of each step may be varied within reason so as to obtain the desired sequence result within a given time and cost and confidence. The apparatus and methods have been described in terms of the structure and conditions required to achieve an intended result in a substantial number of the wells but the skilled person will appreciate that this result will not be achieved in every well due to errors, quality variations in the elements and statistical variation.

The invention claimed is:

1. An array for amplification and sequencing of template polynucleotides, the array comprising:
   a plurality of wells wherein each well is exposed to an ISFET;
   a plurality of capture beads, wherein each capture bead comprises a single template binding site, wherein the wells and capture beads are relatively sized so that only one bead will fit into each well;
   a removable seal arranged to cover the wells and isolate each well from adjacent wells; and
   a heating element.

2. The array according to claim 1, wherein each bead comprises a single immobilised oligonucleotide.

3. The array according to claim 2, wherein the beads are Streptavidin beads and the oligonucleotides are biotin-conjugated oligonucleotides.

4. The array according to claim 1, wherein the beads are fabricated from any one of inorganics, natural polymers, and synthetic polymers.

5. The array according to claim 4, wherein the beads are fabricated from any one of cellulose, cellulose derivatives, glass silica, cross-linked dextrans, agarose gel and polystyrene.

6. The array according to claim 1, wherein the beads provide covalent attachment.

7. The array according to claim 1, wherein the beads are magnetic.

8. The array according to claim 1, wherein the beads are provided with chemical groups that are bound to the surface of the bead to enable the attachment of oligonucleotides.

9. The array according to claim 1, wherein the removable seal is a liquid.

10. The array according to claim 1 wherein the removable seal is a flexible membrane.

11. The array according to claim 10, wherein the seal comprises an adhesive.

12. The array according to claim 1, wherein the heating element is a resistive heating element.

13. The array according to claim 1, further comprising a temperature sensor.

14. The array according to claim 9, wherein the removable seal is a mineral oil.

* * * * *